United States Patent
Powell, Jr.

(10) Patent No.: US 10,844,117 B2
(45) Date of Patent: Nov. 24, 2020

(54) HUMAN ALPHA-FOLATE RECEPTOR CHIMERIC ANTIGEN RECEPTOR

(71) Applicant: The Trustees of the University of Pennsylvania, Philadelphia, PA (US)

(72) Inventor: Daniel J. Powell, Jr., Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/449,274

(22) Filed: Mar. 3, 2017

(65) Prior Publication Data

US 2017/0240630 A1  Aug. 24, 2017

Related U.S. Application Data

(62) Division of application No. 14/432,664, filed as application No. PCT/US2013/063282 on Oct. 3, 2013, now Pat. No. 9,598,489.

(60) Provisional application No. 61/710,493, filed on Oct. 5, 2012.

(51) Int. Cl.
*C07K 16/46* (2006.01)
*C07K 16/22* (2006.01)
*C07K 16/28* (2006.01)
*C07K 14/725* (2006.01)

(52) U.S. Cl.
CPC .......... *C07K 16/28* (2013.01); *C07K 14/7051* (2013.01); *C07K 16/2803* (2013.01); *C07K 2317/21* (2013.01); *C07K 2317/55* (2013.01); *C07K 2317/622* (2013.01); *C07K 2319/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,567 A | 3/1989 | Cabilly et al. |
| 5,199,942 A | 4/1993 | Gillis et al. |
| 5,225,539 A | 7/1993 | Winter |
| 5,229,275 A | 7/1993 | Goroff et al. |
| 5,350,674 A | 9/1994 | Boenisch et al. |
| 5,399,346 A | 3/1995 | Anderson et al. |
| 5,413,923 A | 5/1995 | Kucherlapati et al. |
| 5,506,126 A | 4/1996 | Seed et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,573,905 A | 11/1996 | Lerner et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,731,168 A | 3/1998 | Carter et al. |
| 5,766,886 A | 6/1998 | Studnicka et al. |
| 5,858,358 A | 1/1999 | June et al. |
| 5,883,223 A | 3/1999 | Gray |
| 5,939,598 A | 8/1999 | Kucherlapati et al. |
| 5,993,434 A | 11/1999 | Dev et al. |
| 6,120,766 A | 9/2000 | Hale et al. |
| 6,181,964 B1 | 1/2001 | Hofmann et al. |
| 6,233,482 B1 | 5/2001 | Hofmann et al. |
| 6,241,701 B1 | 6/2001 | Hofmann et al. |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,516,223 B2 | 2/2003 | Hofmann et al. |
| 6,534,055 B1 | 3/2003 | June et al. |
| 6,548,640 B1 | 4/2003 | Winter |
| 6,567,694 B2 | 5/2003 | Hayakawa et al. |
| 6,678,556 B1 | 1/2004 | Nolan et al. |
| 6,692,964 B1 | 2/2004 | June et al. |
| 6,797,514 B2 | 9/2004 | Berenson et al. |
| 6,867,041 B2 | 3/2005 | Berenson et al. |

(Continued)

FOREIGN PATENT DOCUMENTS

| EP | 239400 A2 | 9/1987 |
|---|---|---|
| EP | 592106 B1 | 11/2004 |

(Continued)

OTHER PUBLICATIONS

Lloyd et al. Protein Engineering, Design & Selection 2009, 22:159-168 (Year: 2009).*
Homach et al. 2011. Int J. Cancer. 129:29355-2944 (Year: 2011).*
International Search Report for PCT/US13/63282 dated Jan. 29, 2014.

(Continued)

*Primary Examiner* — Michael D Pak
(74) *Attorney, Agent, or Firm* — Saul Ewing Arnstein & Lehr LLP; Kathryn Doyle

(57) ABSTRACT

The invention provides compositions and methods for treating ovarian cancer. Specifically, the invention relates to administering a genetically modified T cell having α-folate receptor (FRα) binding domain and CD27 costimulatory domain to treat ovarian cancer. In an embodiment, the FRα binding domain is fully human, thereby preventing a host immune response.

21 Claims, 13 Drawing Sheets

Specification includes a Sequence Listing.

(56) References Cited

U.S. PATENT DOCUMENTS

| | | | |
|---|---|---|---|
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,171,264 B1 | 1/2007 | Hofmann et al. |
| 7,172,869 B2 | 2/2007 | June et al. |
| 7,173,116 B2 | 2/2007 | Fewell et al. |
| 7,175,843 B2 | 2/2007 | June et al. |
| 7,232,566 B2 | 6/2007 | June et al. |
| 2004/0014645 A1 | 1/2004 | Draghia-Akli et al. |
| 2004/0059285 A1 | 3/2004 | Mathiesen et al. |
| 2004/0092907 A1 | 5/2004 | Mathiesen et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0052630 A1 | 3/2005 | Smith et al. |
| 2005/0070841 A1 | 3/2005 | Mathiesen et al. |
| 2005/0215770 A1 | 9/2005 | Bell et al. |
| 2005/0232919 A1 | 10/2005 | Grasso et al. |
| 2006/0034810 A1 | 2/2006 | Riley et al. |
| 2006/0121005 A1 | 6/2006 | Berenson et al. |
| 2006/0239910 A1 | 10/2006 | Nicolaides et al. |
| 2007/0128708 A1 | 6/2007 | Gamelin et al. |
| 2008/0260812 A1 | 10/2008 | Matsuyama et al. |
| 2009/0274697 A1 | 11/2009 | Grasso et al. |
| 2009/0324594 A1 | 12/2009 | Nicolaides et al. |
| 2010/0055034 A1 | 3/2010 | Martin et al. |
| 2014/0050708 A1 | 2/2014 | Powell et al. |
| 2015/0110760 A1 | 4/2015 | Sentman et al. |

FOREIGN PATENT DOCUMENTS

| | | |
|---|---|---|
| EP | 519596 B1 | 2/2005 |
| WO | 9109967 A1 | 7/1991 |
| WO | 9110741 A1 | 7/1991 |
| WO | 9317105 A1 | 9/1993 |
| WO | 9633735 A1 | 10/1996 |
| WO | 9634096 A1 | 10/1996 |
| WO | 9816654 A1 | 4/1998 |
| WO | 9824893 A2 | 6/1998 |
| WO | 9846645 A2 | 10/1998 |
| WO | 9850433 A2 | 11/1998 |
| WO | 0129058 A1 | 4/2001 |
| WO | 0196584 A2 | 12/2001 |
| WO | 0208263 A2 | 1/2002 |
| WO | 2011106528 A1 | 9/2011 |
| WO | 2012079000 A1 | 6/2012 |
| WO | 2012099973 A2 | 7/2012 |
| WO | 2012127464 A2 | 9/2012 |

OTHER PUBLICATIONS

Baca, et al., "Antibody Humanization Using Monovalent Phage Display", J. Biol. Chem., 272(16):10678-84 (1997).

Berg, et al., "Selective expansion of a peripheral blood CD8+ memory T cell subset expressing both granzyme B and L-selectin during primary viral infection in renal allograft recipients", Transplant Proc. 30(8):3975-3977, 1998.

Bierer, et al., "Cyclosporin A and FK506: molecular mechanisms of immunosuppression and probes for transplantation biology", Curr. Opin. Immun. 5:763-773, 1993.

Bird, et al., "Single-chain antigen-binding proteins." 1988, Science 242:423-426.

Caldas, et al., "Design and synthesis of germline-based hemi-humanized single-chain Fv against the CD18 surface antigen", Protein Eng., 13(5):353-60 (2000).

Carter, et al., "Humanization of an anti-p185HER2 antibody for human cancer therapy.", Proc. Natl. Acad. Sci. USA, 39:4285-89 (1992).

Chothia, et al., "Canonical structures for the hypervariable regions of immunoglobulins.", J. Mol. Biol., 196:901-17 (1987) (abstract).

Clackson, et al., "Making antibody fragments using phage display libraries", Nature, 352:624-628 (1991) (abstract).

Cougot,, et al., "Cap-tabolism", Trends in Biochem. Sci., 29:436-444 (2001) (abstract).

Couto, et al., "Anti-BA46 Monoclonal Antibody Mc3: Humanization Using a Novel Positional Consensus and in Vivo and in Vitro Characterization.", Cancer Res., 55(8):1717-22 (1995).

Couto, et al., "Designing Human Consensus Antibodies with Minimal Positional Templates", Cancer Res., 55 (23 Supp):5973s-5977s (1995).

Croft, "Co-stimulatory members of the TNFR family: Keys to Effective T-Cell Immunity?", 2003, Nature 3:609-620.

Duchosal, et al., "Immunization of hu-PBL-SCID mice and the rescue of human monoclonal Fab fragments through combinatorial libraries", Nature, 355:258-262 (1992).

Elango, et al., "Optimized transfection of mRNA transcribed from a d(A/T)100 tail-containing vector", Biochim. Biophys. Res. Commun., 330:958-966 (2005) (abstract).

Ertl, et al., "Considerations for the clinical application of chimeric antigen receptor T cells: observations from a recombinant DNA Advisory Committee Symposium held Jun. 15, 2010", 2011, Cancer Res, 71:3175-81.

Figini, et al., "Panning phage antibody libraries on cells: isolation of human Fab fragments against ovarian carcinoma using guided selection.", 1998. Cancer Res. 991-996.

Garland, et al., "The use of Teflon cell culture bags to expand functionally active CD8+ cytotoxic T lymphocytes", J. Immunol Meth. 227(1-2):53-63, 1999.

Griffith, et al., "Human anti-self antibodies with high specificity from phage display libraries", EMBO J., 12:725-734 (1993).

Haanen, et al., "Selective expansion of cross-reactive CD8(+) memory T cells by viral variants.", J. Exp. Med. 190(9):1319-1328, 1999.

Henderson, et al., "Comparison of the effects of FK-506, cyclosporin A and rapamycin on IL-2 production", Immun. 73:316-321,1991.

Hoogenboom, et al., "By-passing immunization. Human antibodies from synthetic repertoires of germline VH gene segments rearranged in vitro", J. Mol. Biol., 227:381-8 (1991) (abstract).

Huston, et al., "Protein engineering of antibody binding sites: recovery of specific activity in an anti-digoxin single-chain Fv analogue produced in *Escherichia coli*", 1988, Proc. Natl. Acad. Sci. USA 85:5879-5883.

Jakobovits, et al., "Germ-line transmission and expression of a human-derived yeast artificial chromosome", Nature, 362:255-258 (1993).

Johnson, et al., "Human antibody engineering", Current Opinion in Structural Biology 3:564-571 (1993).

Jones, et al., "Replacing the complementarity-determining regions in a human antibody with those from a mouse", Nature, 321:522-525 (1986).

Junghans, "Strategy escalation: an emerging paradigm for safe clinical development of T cell gene therapies", 2010, Journal of Translational Medicine, 8:55.

Kandalaft, et al., "A phase I clinical trial of adoptive transfer of folate receptor-alpha redirected autologous T cells for recurrent ovarian cancer.", 2012, Journal of Translational Medicine 10:157-166.

Levine, et al., "Effects of CD28 costimulation on long-term proliferation of CD4+ T cells in the absence of exogenous feeder cells", 1997. J. Immunology. 5921-30.

Liu, et al., "Calcineurin is a common target of cyclophilin-cyclosporin A and FKBP-FK506 complexes", Cell 66:807-815, 1991.

Lonberg, et al., "Human antibodies from transgenic mice.", Int. Rev. Immunol., 13:65-93 (1995).

Marks, et al., "By-passing immunization. Human antibodies from V-gene libraries displayed on phage", J. Mol. Biol. 222:581-597 (1991).

(56) References Cited

OTHER PUBLICATIONS

McCafferty, et al., "Phage antibodies: filamentous phage displaying antibody variable domains", Nature, 348:552-553 (1990)93).
Morea, et al., "Antibody modeling: implications for engineering and design", Methods, 20(3):267-79 (2000).
Mumtaz, "Design of liposomes for circumventing the reticuloendothelial cells", 1991 Glycobiology 5: 505-10.
Nacheva, et al., "Preventing nondesired RNA-primed RNA extension catalyzed by T7 RNA polymerase", Eur. J. Biochem., 270:1485-65 (2003).
Nishikawa, et al., "Nonviral vectors in the new millennium: delivery barriers in gene transfer", Hum. Gene Ther., 12(8):861-70 (2001) (abstract).
Padlan, "A possible procedure for reducing the immunogenicity of antibody variable domains while preserving their ligand-binding properties", 1991, Molecular Immunology, 28(4/5):489-498.
Pedersen, et al., "Comparison of surface accessible residues in human and murine immunoglobulin Fv domains. Implication for humanization of murine antibodies.", J. Mol. Biol., 235(3):959-73 (1994).
Powell, "Costimulation by CD27, not CD28, Significantly Augments the Survival of Genetically Redirected Human T Cells in Vivo", 2011, J. of Immunotherapy 9:680.
Presta, et al., "Humanization of an antibody directed against IgE", J. Immunol., 151:2623-32 (1993).
Riechmann, et al., "Reshaping human antibodies for therapy", Nature, 332:323-327 (1988).
Roder, et al., "The EBV-hybridoma technique", Methods Enzymol., 121:140-167 (1986).
Roguska, et al., "A comparison of two murine monoclonal antibodies humanized by CDR-grafting and variable domain resurfacing", Protein Eng., 9(10):895-904 (1996).
Roguska, et al., "Humanization of murine monoclonal antibodies through variable domain resurfacing", PNAS, 91:969-973 (1994).
Rosenberg, et al., "Use of tumor-infiltrating lymphocytes and interleukin-2 in the immunotherapy of patients with metastatic melanoma. A preliminary report.", New Eng. J. of Med. 319:1676-80, 1988).
Sandhu, "A rapid procedure for the humanization of monoclonal antibodies.", Gene, 150(2):409-10(1994).
Schenborn, et al., "A novel transcription property of SP6 and T7 RNA polymerases: dependence on template structure", Nuc. Acids Res., 13:6223-36 (1985).
Sims, et al., "A humanized CD18 antibody can block function without cell destruction", J. Immunol., 151:2296-2308 (1993).
Song, et al., "In vivo persistence, tumor localization, and antitumor activity of CAR-engineered T cells is enhanced by costimulatory signaling through CD137 (4-1BB)", 2011, Cancer Res. Jul. 1;71(13):4617-273-60.
Song et al., "CD27 costimulation augments the survival and antitumor activity of redirected human T cells in vivo." 2012, Blood;119(3):696-706.
Stepinski., et al., "Synthesis and properties of mRNAs containing the novel "anti-reverse" cap analogs 7-methyl(3'-0-methyl)GpppG and 7-methyl(3'-deoxy)GpppG", RNA, 7:1468-95 (2001).
Studnicka, et al., "Human-engineered monoclonal antibodies retain full specific binding activity by preserving non-CDR complementarity-modulating residues", Protein Engineering, 7(6):805-814 (1994).
Tan, et al., ""Superhumanized" antibodies: reduction of immunogenic potential by complementarity-determining region grafting with human germline sequences: application to an anti-CD28", J. Immunol., 169:1119-25 (2002).
Ui-Tei, et al., "Sensitive assay of RNA interference in *Drosophila* and Chinese hamster cultured cells using firefly luciferase gene as target.", 2000 FEBS Letters 479: 79-82.
Vaughan, et al., "Human antibodies with sub-nanomolar affinities isolated from a large non-immunized phage display library", Nature Biotech., 14:309-14 (1996) (abstract).
Verhoeyen, et al., "Reshaping human antibodies: grafting an antilysozyme activity", Science, 239:1534-1536 (1988).
Wu, et al., "Humanization of a murine monoclonal antibody by simultaneous optimization of framework and CDR residues.", J. Mol. Biol., 294:151-162 (1999).
Zhao, et al., "Multiple injections of electroporated autologous T cells expressing a chimeric antigen receptor mediate regression of human disseminated tumor.", 2010. Can Res. 70(22):9053-9061.

* cited by examiner

9A

| % CAR Expression 12 Hrs Post Electroporation | | | |
|---|---|---|---|
| | 5ug | 10ug | 20ug |
| C4 (αFR) | 86 | 97 | 97 |
| C4 (αHuman IgG) | 98 | 99 | 98 |
| CD19 (αMouse IgG) | 92 | 98 | 97 |

| % CAR Expression 24 Hrs Post Electroporation | | | |
|---|---|---|---|
| | 5ug | 10ug | 20ug |
| C4 (αFR) | 96 | 98 | 98 |
| C4 (αHuman IgG) | 99 | 99 | 98 |
| CD19 (αMouse IgG) | 96 | 99 | 98 |

| % CAR Expression 48 Hrs Post Electroporation | | | |
|---|---|---|---|
| | 5ug | 10ug | 20ug |
| C4 (αFR) | 90 | 97 | 98 |
| C4 (αHuman IgG) | 99 | 98 | 99 |
| CD19 (αMouse IgG) | 95 | 99 | 99 |

| % CAR Expression 72 Hrs Post Electroporation | | | |
|---|---|---|---|
| | 5ug | 10ug | 20ug |
| C4 (αFR) | 90 | 95 | 94 |
| C4 (αHuman IgG) | 98 | 99 | 94 |
| CD19 (αMouse IgG) | 90 | 98 | 96 |

9B

| Viability 12 Hrs Post Electroporation (% of Non-Electroporated) | | | | |
|---|---|---|---|---|
| | 0ug | 5ug | 10ug | 20ug |
| C4 (aFR) | 83 | 73 | 66 | 65 |
| C4 (aHuman IgG) | 83 | 75 | 71 | 69 |
| CD19 (aMouse IgG) | 83 | 77 | 70 | 50 |

FIGS. 9A-9B

SEQUENCE LISTING

<160> NUMBER OF SEQ ID NOS: 24

<210> SEQ ID NO 1
<211> LENGTH: 497

```
<212> TYPE: PRT
<213> ORGANISM: Homo sapiens
<220> FEATURE:
<221> NAME/KEY: misc_feature
<223> OTHER INFORMATION: C4-CD27CD3z-CAR

<400> SEQUENCE: 1
```

Met Ala Leu Pro Val Thr Ala Leu Leu Leu Pro Leu Ala Leu Leu Leu
1               5                   10                  15

His Ala Ala Arg Pro Gly Ser Gln Leu Val Glu Ser Gly Gly Gly Leu
            20                  25                  30

Val Gln Pro Gly Arg Ser Leu Arg Leu Ser Cys Thr Thr Ser Gly Phe
        35                  40                  45

Thr Phe Gly Asp Tyr Ala Met Ile Trp Ala Arg Gln Ala Pro Gly Lys
    50                  55                  60

Gly Leu Glu Trp Val Ser Ser Ile Ser Ser Ser Ser Tyr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Glu Arg Tyr Asp Phe Trp Ser Gly Met
        115                 120                 125

Asp Val Trp Gly Lys Gly Thr Thr Val Thr Val Ser Ser Gly Gly Gly
    130                 135                 140

Gly Ser Gly Gly Gly Gly Ser Gly Gly Ser Ala Gln Ser Ala Leu Thr
145                 150                 155                 160

Gln Pro Ala Ser Val Ser Gly Ser Pro Gly Gln Ser Ile Thr Ile Ser
                165                 170                 175

Cys Thr Gly Thr Ser Ser Asp Val Gly Ser Tyr Asn Leu Val Ser Trp
            180                 185                 190

Tyr Gln Gln His Pro Gly Lys Ala Pro Lys Leu Met Ile Tyr Glu Gly
        195                 200                 205

Ser Lys Arg Pro Ser Gly Val Ser Asn Arg Phe Ser Gly Ser Lys Ser
    210                 215                 220

Gly Asn Ala Ala Ser Leu Thr Ile Ser Gly Leu Gln Ala Glu Asp Glu
225                 230                 235                 240

Ala Asp Tyr Tyr Cys Gln Ser Tyr Asp Ser Ser Leu Ser Val Val Phe
                245                 250                 255

Gly Gly Gly Thr Lys Leu Thr Val Leu Gly Ala Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Gln Arg Arg Lys Tyr Arg Ser Asn Lys Gly Glu Ser Pro Val Glu
            340                 345                 350

Pro Ala Glu Pro Cys Arg Tyr Ser Cys Pro Arg Glu Glu Glu Gly Ser
        355                 360                 365

Thr Ile Pro Ile Gln Glu Asp Tyr Arg Lys Pro Glu Pro Ala Cys Ser
    370                 375                 380

Pro Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
            405                 410                 415

Tyr Asp Val Leu Asp Lys Arg Arg Gly Arg Asp Pro Glu Met Gly Gly
        420                 425                 430

Lys Pro Arg Arg Lys Asn Pro Gln Glu Gly Leu Tyr Asn Glu Leu Gln
    435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
            485                 490                 495

Arg

<210> SEQ ID NO 2
<211> LENGTH: 495
<212> TYPE: PRT
<213> ORGANISM: Homo sapiens
<220> FEATURE:
<221> NAME/KEY: misc_feature
<223> OTHER INFORMATION: C4-CD28CD3z-CAR

<400> SEQUENCE: 2

Met Ala Leu Pro Val Thr Ala Leu Leu Leu Pro Leu Ala Leu Leu Leu
1               5                   10                  15

His Ala Ala Arg Pro Gly Ser Gln Leu Val Glu Ser Gly Gly Gly Leu
            20                  25                  30

Val Gln Pro Gly Arg Ser Leu Arg Leu Ser Cys Thr Thr Ser Gly Phe
        35                  40                  45

Thr Phe Gly Asp Tyr Ala Met Ile Trp Ala Arg Gln Ala Pro Gly Lys
    50                  55                  60

Gly Leu Glu Trp Val Ser Ser Ile Ser Ser Ser Ser Tyr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Glu Arg Tyr Asp Phe Trp Ser Gly Met
        115                 120                 125

Asp Val Trp Gly Lys Gly Thr Thr Val Thr Val Ser Ser Gly Gly Gly
    130                 135                 140

Gly Ser Gly Gly Gly Gly Ser Gly Gly Ser Ala Gln Ser Ala Leu Thr
145                 150                 155                 160

Gln Pro Ala Ser Val Ser Gly Ser Pro Gly Gln Ser Ile Thr Ile Ser
                165                 170                 175

Cys Thr Gly Thr Ser Ser Asp Val Gly Ser Tyr Asn Leu Val Ser Trp
            180                 185                 190

Tyr Gln Gln His Pro Gly Lys Ala Pro Lys Leu Met Ile Tyr Glu Gly
        195                 200                 205

Ser Lys Arg Pro Ser Gly Val Ser Asn Arg Phe Ser Gly Ser Lys Ser
    210                 215                 220

Gly Asn Ala Ala Ser Leu Thr Ile Ser Gly Leu Gln Ala Glu Asp Glu
225                 230                 235                 240

```
Ala Asp Tyr Tyr Cys Gln Ser Tyr Asp Ser Ser Leu Ser Val Val Phe
                245                 250                 255

Gly Gly Gly Thr Lys Leu Thr Val Leu Gly Ala Ser Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
                340                 345                 350

Met Asn Met Thr Pro Arg Arg Pro Gly Pro Thr Arg Lys His Tyr Gln
                355                 360                 365

Pro Tyr Ala Pro Pro Arg Asp Phe Ala Ala Tyr Arg Ser Ile Asp Arg
            370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
            450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 3
<211> LENGTH: 449
<212> TYPE: PRT
<213> ORGANISM: Homo sapiens
<220> FEATURE:
<221> NAME/KEY: misc_feature
<223> OTHER INFORMATION: C4-CD3z-CAR

<400> SEQUENCE: 3

Met Ala Leu Pro Val Thr Ala Leu Leu Leu Pro Leu Ala Leu Leu Leu
1               5                   10                  15

His Ala Ala Arg Pro Gly Ser Gln Leu Val Glu Ser Gly Gly Gly Leu
                20                  25                  30

Val Gln Pro Gly Arg Ser Leu Arg Leu Ser Cys Thr Thr Ser Gly Phe
            35                  40                  45

Thr Phe Gly Asp Tyr Ala Met Ile Trp Ala Arg Gln Ala Pro Gly Lys
    50                  55                  60

Gly Leu Glu Trp Val Ser Ser Ile Ser Ser Ser Ser Tyr Ile Tyr Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
```

```
                100                 105                 110
Ala Val Tyr Tyr Cys Ala Arg Glu Arg Tyr Asp Phe Trp Ser Gly Met
            115                 120                 125
Asp Val Trp Gly Lys Gly Thr Thr Val Thr Val Ser Ser Gly Gly Gly
        130                 135                 140
Gly Ser Gly Gly Gly Ser Gly Gly Ser Ala Gln Ser Ala Leu Thr
145                 150                 155                 160
Gln Pro Ala Ser Val Ser Gly Ser Pro Gly Gln Ser Ile Thr Ile Ser
                165                 170                 175
Cys Thr Gly Thr Ser Ser Asp Val Gly Ser Tyr Asn Leu Val Ser Trp
            180                 185                 190
Tyr Gln Gln His Pro Gly Lys Ala Pro Lys Leu Met Ile Tyr Glu Gly
        195                 200                 205
Ser Lys Arg Pro Ser Gly Val Ser Asn Arg Phe Ser Gly Ser Lys Ser
    210                 215                 220
Gly Asn Ala Ala Ser Leu Thr Ile Ser Gly Leu Gln Ala Glu Asp Glu
225                 230                 235                 240
Ala Asp Tyr Tyr Cys Gln Ser Tyr Asp Ser Ser Leu Ser Val Val Phe
                245                 250                 255
Gly Gly Gly Thr Lys Leu Thr Val Leu Gly Ala Ser Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Arg Val Lys Phe Ser Arg Ser Ala Asp Ala Pro Ala Tyr Lys Gln
            340                 345                 350
Gly Gln Asn Gln Leu Tyr Asn Glu Leu Asn Leu Gly Arg Arg Glu Glu
        355                 360                 365
Tyr Asp Val Leu Asp Lys Arg Arg Gly Arg Asp Pro Glu Met Gly Gly
    370                 375                 380
Lys Pro Arg Arg Lys Asn Pro Gln Glu Gly Leu Tyr Asn Glu Leu Gln
385                 390                 395                 400
Lys Asp Lys Met Ala Glu Ala Tyr Ser Glu Ile Gly Met Lys Gly Glu
                405                 410                 415
Arg Arg Arg Gly Lys Gly His Asp Gly Leu Tyr Gln Gly Leu Ser Thr
            420                 425                 430
Ala Thr Lys Asp Thr Tyr Asp Ala Leu His Met Gln Ala Leu Pro Pro
        435                 440                 445
Arg

<210> SEQ ID NO 4
<211> LENGTH: 21
<212> TYPE: PRT
<213> ORGANISM: Homo sapiens
<220> FEATURE:
<221> NAME/KEY: misc_feature
<223> OTHER INFORMATION: CD8a leader

<400> SEQUENCE: 4

Met Ala Leu Pro Val Thr Ala Leu Leu Leu Pro Leu Ala Leu Leu Leu
```

His Ala Ala Arg Pro
            20

<210> SEQ ID NO 5
<211> LENGTH: 243
<212> TYPE: PRT
<213> ORGANISM: Homo sapiens
<220> FEATURE:
<221> NAME/KEY: misc_feature
<223> OTHER INFORMATION: C4 scFv

<400> SEQUENCE: 5

Gln Leu Val Glu Ser Gly Gly Gly Leu Val Gln Pro Gly Arg Ser Leu
1               5                   10                  15

Arg Leu Ser Cys Thr Thr Ser Gly Phe Thr Phe Gly Asp Tyr Ala Met
            20                  25                  30

Ile Trp Ala Arg Gln Ala Pro Gly Lys Gly Leu Glu Trp Val Ser Ser
        35                  40                  45

Ile Ser Ser Ser Ser Tyr Ile Tyr Tyr Ala Asp Ser Val Lys Gly
    50                  55                  60

Arg Phe Thr Ile Ser Arg Asp Asn Ala Lys Asn Ser Leu Tyr Leu Gln
65                  70                  75                  80

Met Asn Ser Leu Arg Ala Glu Asp Thr Ala Val Tyr Tyr Cys Ala Arg
                85                  90                  95

Glu Arg Tyr Asp Phe Trp Ser Gly Met Asp Val Trp Gly Lys Gly Thr
            100                 105                 110

Thr Val Thr Val Ser Ser Gly Gly Gly Gly Ser Gly Gly Gly Gly Ser
            115                 120                 125

Gly Gly Ser Ala Gln Ser Ala Leu Thr Gln Pro Ala Ser Val Ser Gly
    130                 135                 140

Ser Pro Gly Gln Ser Ile Thr Ile Ser Cys Thr Gly Thr Ser Ser Asp
145                 150                 155                 160

Val Gly Ser Tyr Asn Leu Val Ser Trp Tyr Gln Gln His Pro Gly Lys
                165                 170                 175

Ala Pro Lys Leu Met Ile Tyr Glu Gly Ser Lys Arg Pro Ser Gly Val
            180                 185                 190

Ser Asn Arg Phe Ser Gly Ser Lys Ser Gly Asn Ala Ala Ser Leu Thr
        195                 200                 205

Ile Ser Gly Leu Gln Ala Glu Asp Glu Ala Asp Tyr Tyr Cys Gln Ser
    210                 215                 220

Tyr Asp Ser Ser Leu Ser Val Val Phe Gly Gly Gly Thr Lys Leu Thr
225                 230                 235                 240

Val Leu Gly

<210> SEQ ID NO 6
<211> LENGTH: 45
<212> TYPE: PRT
<213> ORGANISM: Homo sapiens
<220> FEATURE:
<221> NAME/KEY: misc_feature
<223> OTHER INFORMATION: CD8a hinge

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

```
Gly Ala Val His Thr Arg Gly Leu Asp Phe Ala Cys Asp
        35                  40                  45

<210> SEQ ID NO 7
<211> LENGTH: 24
<212> TYPE: PRT
<213> ORGANISM: Homo sapiens
<220> FEATURE:
<221> NAME/KEY: misc_feature
<223> OTHER INFORMATION: CD8a transmembrane

<400> SEQUENCE: 7

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 8
<211> LENGTH: 27
<212> TYPE: PRT
<213> ORGANISM: Homo sapiens
<220> FEATURE:
<221> NAME/KEY: misc_feature
<223> OTHER INFORMATION: CD28 transmembrane

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 48
<212> TYPE: PRT
<213> ORGANISM: Homo sapiens
<220> FEATURE:
<221> NAME/KEY: misc_feature
<223> OTHER INFORMATION: CD27 Intracellular domain

<400> SEQUENCE: 9

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 10
<211> LENGTH: 41
<212> TYPE: PRT
<213> ORGANISM: Homo sapiens
<220> FEATURE:
<221> NAME/KEY: misc_feature
<223> OTHER INFORMATION: CD28 Intracellular domain

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 11
<211> LENGTH: 112
<212> TYPE: PRT
<213> ORGANISM: Homo sapiens
<220> FEATURE:
<221> NAME/KEY: misc_feature
<223> OTHER INFORMATION: CD3 zeta

<400> SEQUENCE: 11

Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 12
<211> LENGTH: 1494
<212> TYPE: DNA
<213> ORGANISM: Homo sapiens
<220> FEATURE:
<221> NAME/KEY: misc_feature
<223> OTHER INFORMATION: C4-CD27CD3z-CAR

<400> SEQUENCE: 12
atggccttac cagtgaccgc cttgctcctg ccgctggcct tgctgctcca cgccgccagg      60
ccgggatccc agctggtgga gtctggggga ggcttggtac agccagggcg gtccctgaga     120
ctctcctgca caacttctgg attcactttt ggtgattatg ctatgatctg ggcccgccag     180
gctccaggga aggggctgga gtgggtctca tccattagta gtagtagtag ttacatatac     240
tacgcagact cagtgaaggg ccgattcacc atctccagag acaacgccaa gaactcactg     300
tatctgcaaa tgaacagcct gagagccgag gacacggctg tgtattactg tgcgagagaa     360
cgatacgatt tttggagtgg aatggacgtc tggggcaaag ggaccacggt caccgtctcg     420
agtggtggag gcggttcagg cggaggtggc tctggcggta gtgcacagtc tgccctgact     480
cagcctgcct ccgtgtctgg gtctcctgga cagtcgatca ccatctcctg cactggaacc     540
agcagtgatg ttgggagtta taaccttgtc cctggtacc aacagcaccc aggcaaagcc      600
cccaaactca tgatttatga gggcagtaag cggccctcag gggtttctaa tcgcttctct     660
ggctccaagt ctggcaacgc ggcctccctg acaatctctg gctccaggc tgaggacgag     720
gctgattatt actgccagtc ctatgacagc agcctgagtg tggtattcgg cggagggacc     780
aagctgaccg tcctaggtgc tagcaccacg acgccagcgc gcgaccacc aacaccggcg      840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca cccttactgc caacgaagg     1020
aaatatagat caaacaaagg agaaagtcct gtggagcctg cagagccttg tcgttacagc    1080
tgccccaggg aggaggaggg cagcaccatc cccatccagg aggattaccg aaaaccggag    1140

```
cctgcctgct cccccagagt gaagttcagc aggagcgcag acgccccgc gtacaagcag    1200 ggccagaacc agctctataa cgagctcaat ctaggacgaa gagaggagta cgatgttttg    1260
gacaagagac gtggccggga ccctgagatg gggggaaagc cgagaaggaa gaaccctcag    1320
gaaggcctgt acaatgaact gcagaaagat aagatggcgg aggcctacag tgagattggg    1380
atgaaaggcg agcgccggag gggcaagggg cacgatggcc tttaccaggg tctcagtaca    1440
gccaccaagg acacctacga cgcccttcac atgcaggccc tgcccctcg ctaa           1494
```

<210> SEQ ID NO 13
<211> LENGTH: 1488
<212> TYPE: DNA
<213> ORGANISM: Homo sapiens
<220> FEATURE:
<221> NAME/KEY: misc_feature
<223> OTHER INFORMATION: C4-CD28CD3z-CAR

<400> SEQUENCE: 13

```
atggccttac cagtgaccgc cttgctcctg ccgctggcct tgctgctcca cgccgccagg      60
ccgggatccc agctggtgga gtctggggga ggcttggtac agccagggcg gtccctgaga    120
ctctcctgca caacttctgg attcactttt ggtgattatg ctatgatctg ggcccgccag    180
gctccaggga aggggctgga gtgggtctca tccattagta gtagtagtag ttacatatac    240
tacgcagact cagtgaaggg ccgattcacc atctccagag acaacgccaa gaactcactg    300
tatctgcaaa tgaacagcct gagagccgag gacacggctg tgtattactg cgagagaa      360 cgatacgatt tttggagtgg aatggacgtc tggggcaaag gaccacggt caccgtctcg    420 agtggtggag gcggttcagg cggaggtggc tctggcggta gtgcacagtc tgccctgact    480
cagcctgcct ccgtgtctgg gtctcctgga cagtcgatca ccatctcctg cactggaacc    540
agcagtgatg ttgggagtta taaccttgtc tcctggtacc aacagcaccc aggcaaagcc    600
cccaaactca tgatttatga gggcagtaag cggccctcag gggtttctaa tcgcttctct    660
ggctccaagt ctggcaacgc ggcctccctg acaatctctg gctccaggc tgaggacgag    720 gctgattatt actgccagtc ctatgacagc agctgagtg tggtattcgg cggagggacc    780
aagctgaccg tcctaggtgc tagcaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgatt tttgggtgct ggtggtggtt    960
ggtggagtcc tggcttgcta tagcttgcta gtaacagtgg cctttattat tttctgggtg    1020
aggagtaaga ggagcaggct cctgcacagt gactacatga catgactcc ccgccgcccc    1080 gggcccaccc gcaagcatta ccagccctat gccccaccac gcgacttcgc agcctatcgc    1140
tccatcgata gagtgaagtt cagcaggagc gcagacgccc ccgcgtacca gcagggccag    1200
aaccagctct ataacgagct caatctagga cgaagagagg agtacgatgt tttggacaag    1260
agacgtggcc gggaccctga gatgggggga aagccgagaa ggaagaaccc tcaggaaggc    1320
ctgtacaatg aactgcagaa agataagatg gcggaggcct acagtgagat tgggatgaaa    1380
ggcgagcgcc ggaggggcaa ggggcacgat ggcctttacc agggtctcag tacagccacc    1440
aaggacacct acgacgccct tcacatgcag gccctgcccc tcgctaa                   1488
```

<210> SEQ ID NO 14
<211> LENGTH: 1350
<212> TYPE: DNA
<213> ORGANISM: Homo sapiens

```
<220> FEATURE:
<221> NAME/KEY: misc_feature
<223> OTHER INFORMATION: C4-CD3z-CAR

<400> SEQUENCE: 14
atggccttac cagtgaccgc cttgctcctg ccgctggcct tgctgctcca cgccgccagg     60
ccgggatccc agctggtgga gtctggggga ggcttggtac agccagggcg gtccctgaga    120
ctctcctgca caacttctgg attcactttt ggtgattatg ctatgatctg ggcccgccag    180
gctccaggga aggggctgga gtgggtctca tccattagta gtagtagtag ttacatatac    240
tacgcagact cagtgaaggg ccgattcacc atctccagag acaacgccaa gaactcactg    300
tatctgcaaa tgaacagcct gagagccgag gacacggctg tgtattactg tgcgagagaa    360
cgatacgatt tttggagtgg aatggacgtc tggggcaaag gaccacggt caccgtctcg    420
agtggtggag gcggttcagg cggaggtggc tctggcggta gtgcacagtc tgccctgact    480
cagcctgcct ccgtgtctgg gtctcctgga cagtcgatca ccatctcctg cactggaacc    540
agcagtgatg ttgggagtta taaccttgtc tcctggtacc aacagcaccc aggcaaagcc    600
cccaaactca tgatttatga gggcagtaag cggccctcag gggtttctaa tcgcttctct    660
ggctccaagt ctggcaacgc ggcctccctg acaatctctg gctccaggc tgaggacgag    720
gctgattatt actgccagtc ctatgacagc agcctgagtg tggtattcgg cggagggacc    780
aagctgaccg tcctaggtgc tagcaccacg acgccagcgc gcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg gcgcccttg    960
gccgggactt gtggggtcct tctcctgtca ctggttatca ccctttactg cagagtgaag   1020
ttcagcagga gcgcagacgc ccccgcgtac aagcagggcc agaaccagct ctataacgag   1080
ctcaatctag gacgaagaga ggagtacgat gttttggaca gagacgtgg ccgggaccct   1140
gagatggggg gaaagccgag aaggaagaac cctcaggaag gcctgtacaa tgaactgcag   1200
aaagataaga tggcggaggc ctacagtgag attgggatga aggcgagcg ccggaggggc   1260
aaggggcacg atggccttta ccagggtctc agtacagcca ccaaggacac ctacgacgcc   1320
cttcacatgc aggccctgcc ccctcgctaa                                   1350

<210> SEQ ID NO 15
<211> LENGTH: 63
<212> TYPE: DNA
<213> ORGANISM: Homo sapiens
<220> FEATURE:
<221> NAME/KEY: misc_feature
<223> OTHER INFORMATION: CD8a leader

<400> SEQUENCE: 15
atggccttac cagtgaccgc cttgctcctg ccgctggcct tgctgctcca cgccgccagg     60
ccg                                                                  63

<210> SEQ ID NO 16
<211> LENGTH: 729
<212> TYPE: DNA
<213> ORGANISM: Homo sapiens
<220> FEATURE:
<221> NAME/KEY: misc_feature
<223> OTHER INFORMATION: C4 scFv

<400> SEQUENCE: 16
cagctggtgg agtctggggg aggcttggta cagccagggc ggtccctgag actctcctgc     60
```

-continued

```
acaacttctg gattcacttt tggtgattat gctatgatct gggcccgcca ggctccaggg    120
aaggggctgg agtgggtctc atccattagt agtagtagta gttacatata ctacgcagac    180
tcagtgaagg gccgattcac catctccaga caacgcca agaactcact gtatctgcaa      240
atgaacagcc tgagagccga ggacacggct gtgtattact gtgcgagaga acgatacgat    300
ttttggagtg gaatggacgt ctggggcaaa gggaccacgg tcaccgtctc gagtggtgga    360
ggcggttcag gcggaggtgg ctctggcggt agtgcacagt ctgccctgac tcagcctgcc    420
tccgtgtctg ggtctcctgg acagtcgatc accatctcct gcactggaac cagcagtgat    480
gttgggagtt ataaccttgt ctcctggtac aacagcacc caggcaaagc ccccaaactc     540
atgatttatg agggcagtaa gcggccctca ggggtttcta atcgcttctc tggctccaag    600
tctggcaacg cggcctccct gacaatctct gggctccagg ctgaggacga ggctgattat    660
tactgccagt cctatgacag cagcctgagt gtggtattcg gcggagggac caagctgacc    720
gtcctaggt                                                            729

<210> SEQ ID NO 17
<211> LENGTH: 135
<212> TYPE: DNA
<213> ORGANISM: Homo sapiens
<220> FEATURE:
<221> NAME/KEY: misc_feature
<223> OTHER INFORMATION: CD8a hinge

<400> SEQUENCE: 17
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg    120
gacttcgcct gtgat                                                     135

<210> SEQ ID NO 18
<211> LENGTH: 72
<212> TYPE: DNA
<213> ORGANISM: Homo sapiens
<220> FEATURE:
<221> NAME/KEY: misc_feature
<223> OTHER INFORMATION: CD8a transmembrane

<400> SEQUENCE: 18
atctacatct gggcgccctt ggccgggact tgtggggtcc ttctcctgtc actggttatc    60 acccttact gc                                                         72

<210> SEQ ID NO 19
<211> LENGTH: 81
<212> TYPE: DNA
<213> ORGANISM: Homo sapiens
<220> FEATURE:
<221> NAME/KEY: misc_feature
<223> OTHER INFORMATION: CD28 transmembrane

<400> SEQUENCE: 19
ttttgggtgc tggtggtggt tggtggagtc ctggcttgct atagcttgct agtaacagtg    60
gcctttatta ttttctgggt g                                              81

<210> SEQ ID NO 20
<211> LENGTH: 144
<212> TYPE: DNA
<213> ORGANISM: Homo sapiens
<220> FEATURE:
<221> NAME/KEY: misc_feature
```

```
<223> OTHER INFORMATION: CD27 Intracellular domain

<400> SEQUENCE: 20
caacgaagga aatatagatc aaacaaagga gaaagtcctg tggagcctgc agagccttgt      60
cgttacagct gccccaggga ggaggagggc agcaccatcc ccatccagga ggattaccga     120
aaaccggagc ctgcctgctc cccc                                            144

<210> SEQ ID NO 21
<211> LENGTH: 123
<212> TYPE: DNA
<213> ORGANISM: Homo sapiens
<220> FEATURE:
<221> NAME/KEY: misc_feature
<223> OTHER INFORMATION: CD28 Intracellular domain

<400> SEQUENCE: 21
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 22
<211> LENGTH: 339
<212> TYPE: DNA
<213> ORGANISM: Homo sapiens
<220> FEATURE:
<221> NAME/KEY: misc_feature
<223> OTHER INFORMATION: CD3 zeta

<400> SEQUENCE: 22
agagtgaagt tcagcaggag cgcagacgcc cccgcgtaca gcagggcca gaaccagctc       60 tataacgagc tcaatctagg acgaagagag gagtacgatg ttttggacaa gacacgtggc    120
cgggaccctg agatggggggg aaagccgaga aggaagaacc ctcaggaagg cctgtacaat   180
gaactgcaga agataagat ggcggaggcc tacagtgaga ttgggatgaa aggcgagcgc     240 cggagggggca aggggcacga tggcctttac caggggtctca gtacagccac caaggacacc   300
tacgacgccc ttcacatgca ggccctgccc cctcgctaa                           339

<210> SEQ ID NO 23
<211> LENGTH: 33
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<223> OTHER INFORMATION: forward primer

<400> SEQUENCE: 23
ataggatccc agctggtgga gtctggggga ggc                                   33

<210> SEQ ID NO 24
<211> LENGTH: 33
<212> TYPE: DNA
<213> ORGANISM: Artificial Sequence
<220> FEATURE:
<223> OTHER INFORMATION: chemically synthesized
<220> FEATURE:
```

| <221> NAME/KEY: misc_feature
| <223> OTHER INFORMATION: reverse primer

<400> SEQUENCE: 24
atagctagca cctaggacgg tcagcttggt ccc                              33

HUMAN ALPHA-FOLATE RECEPTOR CHIMERIC ANTIGEN RECEPTOR

CROSS-REFERENCE TO RELATED APPLICATIONS

This application is a divisional continuation of U.S. patent application Ser. No. 14/432,664, filed Mar. 31, 2015, issued as U.S. Pat. No. 9,598,489, which is a U.S. national phase application filed under 35 U.S.C. § 371 claiming benefit to International Patent Application No. PCT/US2013/063282 filed on Oct. 3, 2013, which is entitled to priority under 35 U.S.C. .sctn.119(e) to U.S. Provisional Application No. 61/710,493, filed Oct. 5, 2012, each of which is hereby incorporated by reference in its entirety.

BACKGROUND OF THE INVENTION

The chimeric antigen receptor (CAR) provides a promising approach for adoptive T-cell immunotherapy for cancer. Commonly, CARs comprise a single chain fragment variable (scFv) of an antibody specific for a tumor associated antigen (TAA) coupled via hinge and transmembrane regions to cytoplasmic domains of T-cell signaling molecules. The most common lymphocyte activation moieties include a T-cell costimulatory (e.g. CD28, CD137, OX40, ICOS, and CD27) domain in tandem with a T-cell triggering (e.g. CD3ζ) moiety. The CAR-mediated adoptive immunotherapy allows CAR-grafted T cells to directly recognize the TAAs on target tumor cells in a non-HLA-restricted manner.

Folate receptor-alpha (FR) is an attractive candidate for targeted biologic therapy of ovarian cancer. Moreover, the common expression of FR on primary and synchronous metastatic disease as well as on recurrent disease suggests that FR-based therapeutic strategies may be helpful for most women with ovarian cancer, whether newly diagnosed with disseminated disease or experiencing disease recurrence. It has been previously demonstrated that incorporation of the CD137 signaling domain in FR-specific CARs thus overcomes the limitation of past CAR approaches by improving the persistence of transferred T cells in vivo, and bolstering their accumulation in tumor and antitumor potency. However, the majority of the CARs reported so far contain a scFv moiety that derived from murine-derived or "humanized" antibodies for specific recognition of TAAs, which might trigger a host immune response and have inherent risks for the production of human anti-mouse antibodies (HAMA).

There is a need in the art for fully human CAR that targets folate receptor. The present invention addresses this unmet need in the art.

BRIEF SUMMARY OF THE INVENTION

The invention includes an isolated nucleic acid sequence encoding a chimeric antigen receptor (CAR), wherein the isolated nucleic acid sequence comprises the human nucleic acid sequence of an α-folate receptor (FRα) binding domain, the nucleic acid sequence of an intracellular domain of a costimulatory molecule, and the nucleic acid sequence of a CD3 zeta signaling domain. In one embodiment, the isolated nucleic acid sequence encodes a CAR comprising the amino acid sequence of SEQ ID NO: 1. In another embodiment, the isolated nucleic acid sequence comprises the nucleic acid sequence of SEQ ID NO: 12. In another embodiment, the FRα binding domain is a human antibody or a FRα-binding fragment thereof. In yet another embodiment, the FRα-binding fragment is a Fab or a scFv. In a further embodiment, the nucleic acid sequence of the FRα binding domain encodes a FRα binding domain comprising the amino acid sequence of SEQ ID NO: 5. In another embodiment, the FRα binding domain comprises the nucleic acid sequence of SEQ ID NO: 16. In yet a further embodiment, the nucleic acid of an intracellular domain of a costimulatory domain encodes a CD27 costimulatory domain comprising the amino acid sequence of SEQ ID NO: 9. In another embodiment, the nucleic acid sequence of the intracellular domain of a costimulatory molecule comprises the nucleic acid sequence of SEQ ID NO: 20. In an additional embodiment, the nucleic acid sequence of CD3 zeta signaling domain encodes a CD3 zeta signaling domain comprising the amino acid sequence of SEQ ID NO: 11. In another embodiment, the nucleic acid sequence of CD3 zeta signaling domain comprises the nucleic acid sequence of SEQ ID NO: 22. In yet a further embodiment, the isolated nucleic acid sequence further comprises the nucleic acid sequence of a transmembrane domain.

Also included in the invention is an isolated chimeric antigen receptor (CAR) comprising a human FRα binding domain, an intracellular domain of a costimulatory molecule, and a CD3 zeta signaling domain. In one embodiment, the CAR comprises the amino acid sequence of SEQ ID NO: 1. In another embodiment, the FRα binding domain is a human antibody or a FRα-binding fragment thereof. In a further embodiment, the FRα-binding fragment is a Fab or a scFv. In an additional embodiment, the FRα binding domain comprises the amino acid sequence of SEQ ID NO: 5. In another embodiment, the intracellular domain of a costimulatory molecule is a CD27 costimulatory domain comprising the amino acid sequence of SEQ ID NO: 9. In another embodiment, the CD3 zeta signaling domain comprises the amino acid sequence of SEQ ID NO: 11. In another embodiment, the isolated CAR further comprises a transmembrane domain.

Also included in the invention is a genetically modified T cell comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain.

The invention additionally includes a vector comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain.

In addition, the invention includes a method for providing anti-tumor immunity in a subject. The method comprises administering to the subject an effective amount of a genetically modified T cell comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain, thereby providing anti-tumor immunity in the subject. In one embodiment, the subject is a human. Further included in the invention is a method for stimulating a T cell-mediated immune response to a cell population or tissue in a subject. The method comprises administering to the subject an effective amount of a genetically modified T cell comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain, thereby stimulating a T cell-mediated immune response in the subject. Additionally included in the invention is a method for treating an ovarian cancer in a subject. The method comprises administering to the subject an effective amount of a genetically modified T cell comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain, thereby treating the ovarian cancer in the subject.

The invention also includes a method for treating cancer in a subject. The method comprises administering to the subject an effective amount of a genetically modified T cell comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain, thereby treating cancer in the subject.

The invention further includes a method of generating a persisting population of genetically engineered T cells in a subject diagnosed with ovarian cancer, the method comprising: administering to the subject an effective amount of a genetically modified T cell comprising an isolated nucleic acid sequence encoding a chimeric antigen receptor (CAR), wherein the isolated nucleic acid sequence comprises the human nucleic acid sequence of a α-folate receptor (FRα) binding domain, the nucleic acid sequence of an intracellular domain of a costimulatory molecule, and the nucleic acid sequence of a CD3 zeta signaling domain, wherein the persisting population of genetically engineered T cells persists in the subject for at least one month after administration. In one embodiment, the persisting population of genetically engineered T cells persists in the human for at least three months after administration.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is a schematic representation depicting C4-based CAR constructs containing the CD3-zeta cytosolic domain alone (C4-z) or in combination with CD28 co-stimulatory module (C4-28z). FIG. 1B is a series of graphs depicting the dual expression of GFP and human FRa-specific CAR.

FIG. 2A is a schematic representation depicting C4-based CAR constructs containing the CD3-zeta cytosolic domain alone (C4-z) or in combination with CD27 co-stimulatory module (C4-27z). FIG. 2B is a series of graphs depicting C4-z and C4-27z CAR expression on both human CD4+ and CD8+ T cells.

FIG. 6A is a series of graphs depicting upregulation of CD137 when C4-27z T cells were incubated with FRa(+) tumor cells, but not FRa(−) cells. FIG. 6B is a series of images depicting CD137 up-regulation in C4-27z CAR T cells.

FIG. 7A is a graph depicting tumor volume compared to time in mice receiving Untransduced (UNT) T cells, C4-z, and C4-27z CAR T cells. Tumors were measured by measured by caliper-based sizing. FIG. 7B is a series of images depicting tumor size in mice based on bioluminescence imaging.

FIGS. 9A-9B are series of tables illustrating that C4 and CD19 control CARS are fully expressed by human cells after electroporation with PDA-C4-27Z and PDA-CD19-27Z IVT RNA. FIG. 9A is a table listing the percentage of C4 and CD19 control CARS expression at 12 hours, 24 hours, 48 hours and 72 hours post electroporation. FIG. 9B is a table listing the viability of C4 and CD19 control CARS at 12 hours post electroporation.

DETAILED DESCRIPTION

Figure 1A:
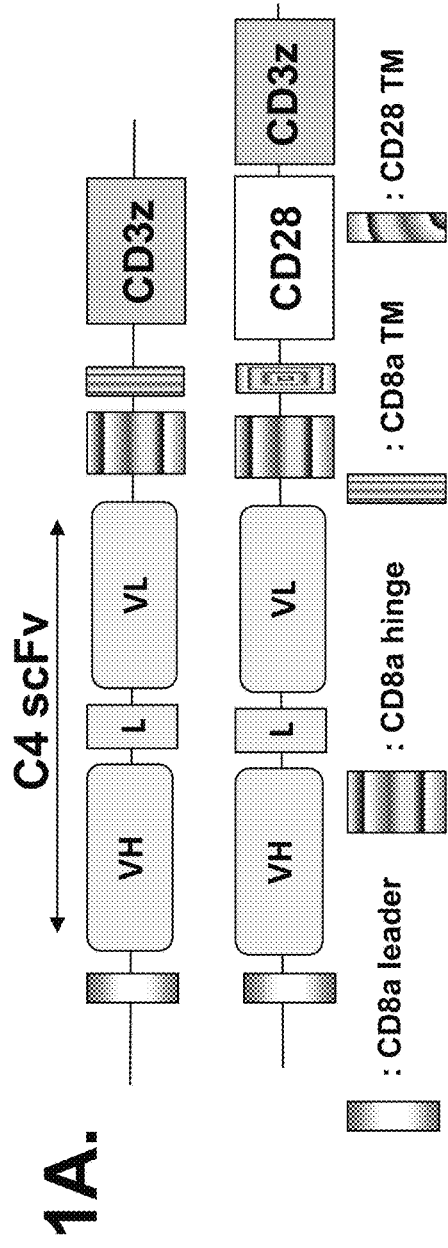
FIGS. 1A-1B are series of images and graphs depicting CAR constructs and co-expression of GFP and fully human FRa-specific CAR on primary human T cells.

The invention relates to compositions and methods for treating cancer including but not limited to ovarian cancer.

The present invention relates to a strategy of adoptive cell transfer of T cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The present invention provides for a compositions where a CAR, or portions thereof, is fully human, thereby minimizing the risk for a host immune response.

The present invention relates generally to the use of T cells genetically modified to stably express a desired CAR. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the CAR can comprise a fully human antibody or antibody fragment. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one embodiment, the transmembrane domain is the CD8α transmembrane domain.

In one embodiment, with respect to the cytoplasmic domain, the CAR of the invention can be designed to comprise the CD28 and CD27 signaling domain by itself or be combined with any other desired cytoplasmic domain(s) useful in the context of the CAR of the invention. However, the invention should not be limited to only CD28 and CD27. Rather, other costimulatory molecules may also be included in the invention. In one embodiment, the cytoplasmic domain of the CAR can be designed to further comprise the signaling domain of CD3-zeta. For example, the cytoplasmic domain of the CAR can include but is not limited to CD3-zeta, CD28, and CD27 signaling modules and combinations thereof. Accordingly, the invention provides CAR T cells and methods of their use for adoptive therapy.

In one embodiment, the CAR T cells of the invention can be generated by introducing a lentiviral vector comprising a desired CAR targeting the α-folate receptor (αFR or FRα) into the cells. For example, the lentiviral vector comprises a CAR comprising anti-FRα, CD8α hinge and transmembrane domain, and CD27 and CD3-zeta signaling domains, into the cells. In one embodiment, the CAR T cells of the invention are able to replicate in vivo resulting in long-term persistence that can lead to sustained tumor control.

In another embodiment, the CAR T cells of the invention can be generated by transfecting an RNA encoding the desired CAR, for example a CAR comprising anti-FRα, CD8α hinge and transmembrane domain, and CD27 and CD3-zeta signaling domains, into the cells. In one embodiment, the CAR is transiently expressed in the genetically modified CAR T cells.

The anti-FRα domain of the CAR of the invention can be any domain that binds to FRα including but not limited to monoclonal antibodies, polyclonal antibodies, antibody fragments, and humanized antibodies. In one embodiment, the anti-FRα domain of the CAR of the invention is a fully human antibody, or fragment thereof. Therefore, as used herein, anti-FRα (or anti-αFR) refers to any composition targeted to FRα. The CAR T cells of the invention are able to replicate in vivo resulting in long-term persistence that can lead to sustained tumor control.

In one embodiment, the invention relates to a CAR comprising a human antibody, or fragments thereof. The invention is based upon the discovery that a CAR comprising an antigen recognition domain comprising a fully human antibody fragment specifically recognize tumor antigens. Therefore, human CARs of the invention can be used to treat cancers and other disorders and avoid the risk of inducing an immune response.

In one embodiment, the invention relates to a CAR comprising a CD27 costimulatory domain. The invention is based upon the discovery that a CAR comprising a CD27 costimulatory domain effectively recognizes and kills antigen-specific tumors. Therefore, CARs comprising CD27 can be used to treat cancers and other disorders.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

The invention includes using T cells expressing an anti-FRα CAR including both CD3-zeta and the CD27 costimulatory domain (also referred to as FRα-specific CAR T cells). In one embodiment, The FRα-specific CAR T cells of the invention can undergo robust in vivo T cell expansion and can establish FRα-specific memory cells that persist at high levels for an extended amount of time in blood and bone marrow. In some instances, the FRα-specific CAR T cells of the invention infused into a patient can eliminate cancerous cells in vivo in patients with epithelial ovarian cancer. However, the invention is not limited to FRα-specific CAR T cells. Rather, the invention includes any antigen binding moiety fused with one or more intracellular domains selected from the group of a CD27 signaling domain, a CD28 signaling domain, a CD3-zeta signal domain, and any combination thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "FRα binding domain" may refer to any FRα specific binding domain, known to one of skilled in the art. In one example, FRα binding domain comprises a single-chain variable fragment (scFv) comprising the variable regions of the heavy ($V_H$) and light chains ($V_L$) of an antibody binding specifically to FRα. Anti-FRα antibodies, antibody fragments, and their variants are well known in the art and fully described in U.S. Patent Publications U.S 20100055034; U.S. 20090324594; U.S. 20090274697; U.S. 20080260812; U.S. 20060239910; U.S. 20050232919; U.S. 20040235108, all of which are incorporated by reference herein in their entirety. In one embodiment, the FRα binding domain is a homologue, a variant, an isomer, or a functional fragment of an anti-FRα antibody. Each possibility represents a separate embodiment of the present invention.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies, human antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer among other diseases. The cancer may be a hematological malignancy, a solid tumor, a primary or a metastasizing tumor. Preferably, the cancer is an epithelial cancer, or in other words, a carcinoma. More preferably, the cancer is epithelial ovarian cancer. Other diseases treatable using the compositions and methods of the invention include viral, bacterial and parasitic infections as well as autoimmune diseases.

In one embodiment, the invention provides a cell (e.g., T cell) engineered to express a CAR wherein the CAR T cell exhibits an antitumor property. In a preferred embodiment, the CAR is a fully human CAR. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is able to redirect antigen recognition based on the antigen binding specificity. An exemplary antigen is FRα because this antigen is expressed on malignant epithelial cells. However, the invention is not limited to targeting FRα. Rather, the invention includes any antigen binding moiety that when bound to its cognate antigen, affects a tumor cell so that the tumor cell fails to grow, is prompted to die, or otherwise is affected so that the tumor burden in a patient is diminished or eliminated. The antigen binding moiety is preferably fused with an intracellular domain from one or more of a costimulatory molecule and a zeta chain. Preferably, the antigen binding moiety is fused with one or more intracellular domains selected from the group of a CD27 signaling domain, a CD28 signaling domain, a CD3-zeta signal domain, and any combination thereof.

In one embodiment, the CAR of the invention comprises a CD27 signaling domain. This is because the present invention is partly based on the discovery that CAR-mediated T-cell responses can be further enhanced with the addition of costimulatory domains. For example, inclusion of the CD27 signaling domain significantly increased antitumor activity to an otherwise identical CAR T cell not engineered to express CD27.

Composition

The present invention provides chimeric antigen receptor (CAR) comprising an extracellular and intracellular domain. In some embodiments, the CAR of the invention is fully human. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding moiety that specifically binds to an antigen on a tumor cell. In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

In a preferred embodiment, the antigen binding moiety portion of the CAR targets an antigen that includes but is not limited to FRα, CD24, CD44, CD133, CD166, epCAM, CA-125, HE4, Oval, estrogen receptor, progesterone receptor, HER-2/neu, uPA, PAI-1, and the like.

The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in one embodiment, the antigen biding domain portion comprises a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-FRα antibodies directed against the human FRα antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A "humanized" antibody retains a similar antigenic specificity as the original antibody, i.e., in the present invention, the ability to bind human FRα. However, using certain methods of humanization, the affinity and/or specificity of binding of the antibody for human FRα may be increased using methods of "directed evolution," as described by Wu et al., J. Mol. Biol., 294:151 (1999), the contents of which are incorporated herein by reference herein in their entirety.

In one embodiment, the antigen binding moiety portion of the CAR of the invention targets FRα. Preferably, the antigen binding moiety portion in the CAR of the invention is a fully human anti-FRα scFV, wherein the nucleic acid sequence of the human anti-FRα scFV comprises the sequence set forth in SEQ ID NO: 16. In one embodiment, the human anti-FRα scFV comprise the nucleic acid sequence that encodes the amino acid sequence of SEQ ID NO: 5. In another embodiment, the human anti-FRα scFV portion of the CAR of the invention comprises the amino acid sequence set forth in SEQ ID NO: 5.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention is the CD8 transmembrane domain. In one embodiment, the CD8 transmembrane domain comprises the nucleic acid sequence of SEQ ID NO: 18. In one embodiment, the CD8 transmembrane domain comprises the nucleic acid sequence that encodes the amino acid sequence of SEQ ID NO: 7. In another embodiment, the CD8 transmembrane domain comprises the amino acid sequence of SEQ ID NO: 7.

In one embodiment, the transmembrane domain in the CAR of the invention is the CD28 transmembrane domain. In one embodiment, the CD28 transmembrane domain comprises the nucleic acid sequence of SEQ ID NO: 19. In one embodiment, the CD28 transmembrane domain comprises the nucleic acid sequence that encodes the amino acid sequence of SEQ ID NO: 8. In another embodiment, the CD28 transmembrane domain comprises the amino acid sequence of SEQ ID NO: 8.

In some instances, the transmembrane domain of the CAR of the invention comprises the CD8 hinge domain. In one embodiment, the CD8 hinge domain comprises the nucleic acid sequence of SEQ ID NO: 17. In one embodiment, the CD8 hinge domain comprises the nucleic acid sequence that encodes the amino acid sequence of SEQ ID NO: 6. In another embodiment, the CD8 hinge domain comprises the amino acid sequence of SEQ ID NO: 6.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD27 as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of CD27. In yet another embodiment, the cytoplasmic domain is designed to comprise the signaling domain of CD3-zeta, the signaling domain of CD28, and the signaling domain of CD27.

In one embodiment, the cytoplasmic domain in the CAR of the invention is designed to comprise the signaling domain of CD27 and the signaling domain of CD3-zeta, wherein the signaling domain of CD27 comprises the nucleic acid sequence set forth in SEQ ID NO: 20 and the signaling domain of CD3-zeta comprises the nucleic acid sequence set forth in SEQ ID NO: 22.

In one embodiment, the cytoplasmic domain in the CAR of the invention is designed to comprise the signaling domain of CD27 and the signaling domain of CD3-zeta, wherein the signaling domain of CD27 comprises the nucleic acid sequence that encodes the amino acid sequence of SEQ ID NO: 9 and the signaling domain of CD3-zeta comprises the nucleic acid sequence that encodes the amino acid sequence of SEQ ID NO: 11.

In one embodiment, the cytoplasmic domain in the CAR of the invention is designed to comprise the signaling domain of CD27 and the signaling domain of CD3-zeta, wherein the signaling domain of CD27 comprises the amino acid sequence set forth in SEQ ID NO: 9 and the signaling domain of CD3-zeta comprises the amino acid sequence set forth in SEQ ID NO: 11.

In one embodiment, the cytoplasmic domain in the CAR of the invention is designed to comprise the signaling domain of CD28 and the signaling domain of CD3-zeta, wherein the signaling domain of CD28 comprises the nucleic acid sequence set forth in SEQ ID NO: 21 and the signaling domain of CD3-zeta comprises the nucleic acid sequence set forth in SEQ ID NO: 22.

In one embodiment, the cytoplasmic domain in the CAR of the invention is designed to comprise the signaling domain of CD28 and the signaling domain of CD3-zeta, wherein the signaling domain of CD28 comprises the nucleic acid sequence that encodes the amino acid sequence of SEQ ID NO: 10 and the signaling domain of CD3-zeta comprises the nucleic acid sequence that encodes the amino acid sequence of SEQ ID NO: 11.

In one embodiment, the cytoplasmic domain in the CAR of the invention is designed to comprise the signaling domain of CD28 and the signaling domain of CD3-zeta, wherein the signaling domain of CD28 comprises the amino acid sequence set forth in SEQ ID NO: 10 and the signaling domain of CD3-zeta comprises the amino acid sequence set forth in SEQ ID NO: 11.

Vectors

The present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD27, CD28 and the like. In some instances, the CAR can comprise any combination of CD3-zeta, CD27, CD28 and the like.

In one embodiment, the CAR of the invention comprises anti-FRα scFv, human CD8 hinge and transmembrane domain, and CD27 and CD3-zeta signaling domains. In one embodiment the anti-FRα scFv is fully human. In one embodiment, the CAR of the invention comprises the nucleic acid sequence set forth in SEQ ID NO: 12. In another embodiment, the CAR of the invention comprises the nucleic acid sequence that encodes the amino acid sequence of SEQ ID NO: 1. In another embodiment, the CAR of the invention comprises the amino acid sequence set forth in SEQ ID NO: 1.

In one embodiment, the CAR of the invention comprises anti-FRα scFv, human CD8 hinge, CD28 transmembrane domain, and CD28 and CD3-zeta signaling domains. In one embodiment the anti-FRα scFv is fully human. In one embodiment, the CAR of the invention comprises the nucleic acid sequence set forth in SEQ ID NO: 13. In another embodiment, the CAR of the invention comprises the nucleic acid sequence that encodes the amino acid sequence of SEQ ID NO: 2. In another embodiment, the CAR of the invention comprises the amino acid sequence set forth in SEQ ID NO: 2.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In another embodiment, the desired CAR can be expressed in the cells by way of transponsons.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, the template for the RNA CAR comprises an extracellular domain comprising an anti-FRα scFv; a transmembrane domain comprising the hinge and transmembrane domain of CD8a; and a cytoplasmic domain comprises the signaling domain of CD3-zeta and the signaling domain of CD27.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transponsons.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: an RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62L$^{hi}$, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a CAR that combines an antigen recognition domain of a specific antibody with an intracellular domain of CD3-zeta, CD28, CD27, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3-zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, FRα-specific CAR T cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, FRα-specific CAR T cells elicit an immune response specific against cells expressing FRα.

While the data disclosed herein specifically disclose lentiviral vector comprising human anti-FRα scFv (e.g. C4 scFv), human CD8α hinge and transmembrane domain, and CD27 and CD3-zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

In one embodiment, the antigen bind moiety portion of the CAR of the invention is designed to treat a particular cancer. FRα is a glycosylphosphatidylinositol-anchored protein that is overexpressed on the surface of cancer cells in a spectrum of epithelial malignancies, but is limited in normal tissue. As such, CARs designed to target FRα can be used to treat any disease or disorders, including but not limited to epithelial cancers, characterized by cells and/or tissues displaying an overexpression of FRα. For example, the CAR designed to target FRα can be used to treat cancers and disorders including but are not limited to ovarian cancer, lung cancer, breast cancer, renal cancer, colorectal cancer, other solid cancers and the like.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of ovarian cancer. In certain embodiments, the cells of the invention are used in the treatment of patients at risk for developing ovarian cancer. Thus, the present invention provides methods for the treatment or prevention of ovarian cancer comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766). Strategies for CART cell dosing and scheduling have been discussed (Ertl et al, 2011, Cancer Res, 71:3175-81; Junghans, 2010, Journal of Translational Medicine, 8:55).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Characterization of T Cells with Fully-Human CAR

The results presented herein describe the preclinical characterization of T cells bearing a fully human CAR that specifically reacts against FRa+ tumor cells in vitro, and causes inhibition of established FR+ tumor after systemic administration of genetically redirected human T cells in mice.

Construction and Expression of Fully Human FRa-Specific CAR

The fully human anti-FRa C4 scFv (Figini et al., Cancer Res. 1998, 58: 991-996) was amplified by PCR from pHEN2-AFRA4 plasmid by using the primers 5'-ata ggatcccagctggtggagtctggggaggc-3' (SEQ ID NO: 23; forward primer, BamH1 site underlined) and 5'-ata gctagcacctaggacggtcagcttggtccc-3' (SEQ ID NO: 24; reverse primer, Nhe1 site underlined) and then cloned into the z-CAR or 28z CAR lentiviral backbone, in which the CAR sequences were preceded in frame by a green fluorescent protein (GFP) sequence followed by the 2A ribosomal skipping sequence (FIG. 1A).

Figure 1B:
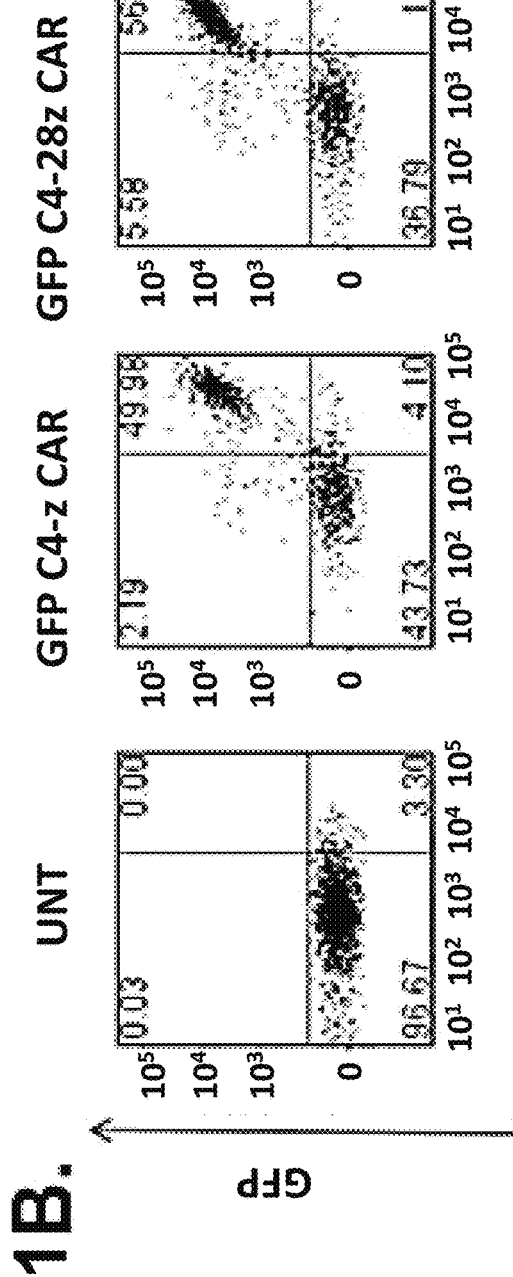

Biotin-SP-conjugated AffiniPure Rabbit Anti-Human IgG (H+L), followed by Streptavidin-APC, were used for human FRa scFv staining on the T cell surface. Bicistronic expression vectors incorporating 2A peptide sequences permitted dual expression of GFP and the C4 CAR (FIG. 1B).

Figures 2A, 2B:
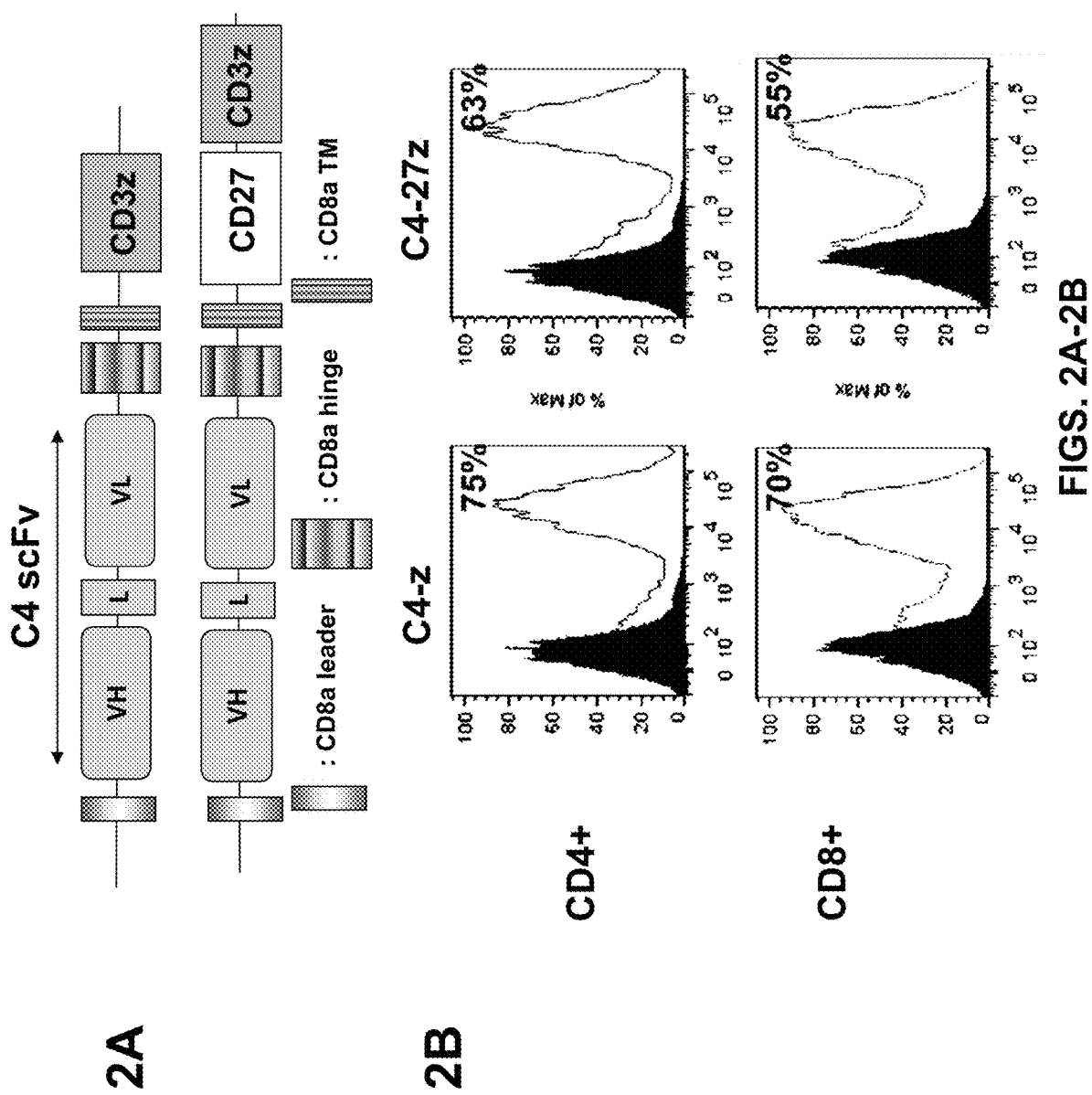
FIGS. 2A-2B are series of images and graphs depicting CAR constructs and C4-z and C4-27z CAR expression.

The human anti-FRa C4 scFv was cloned into the -z CAR and -27z CAR constructs without GFP. The generated construct was composed of the C4 scFv linked to a CD8a hinge and transmembrane followed by CD27 and CD3-zeta intracellular signaling motif (FR-27z; FIG. 2A), or CD3z alone (C4-z). Both primary human CD4+ and CD8 T+ cells efficiently expressed C4-specific CARs as measured by flow cytometry (FIG. 2B).

Costimulated Fully Human FR C4 CAR T Cells Exert Enhanced Reactivity In Vitro

Figure 3:
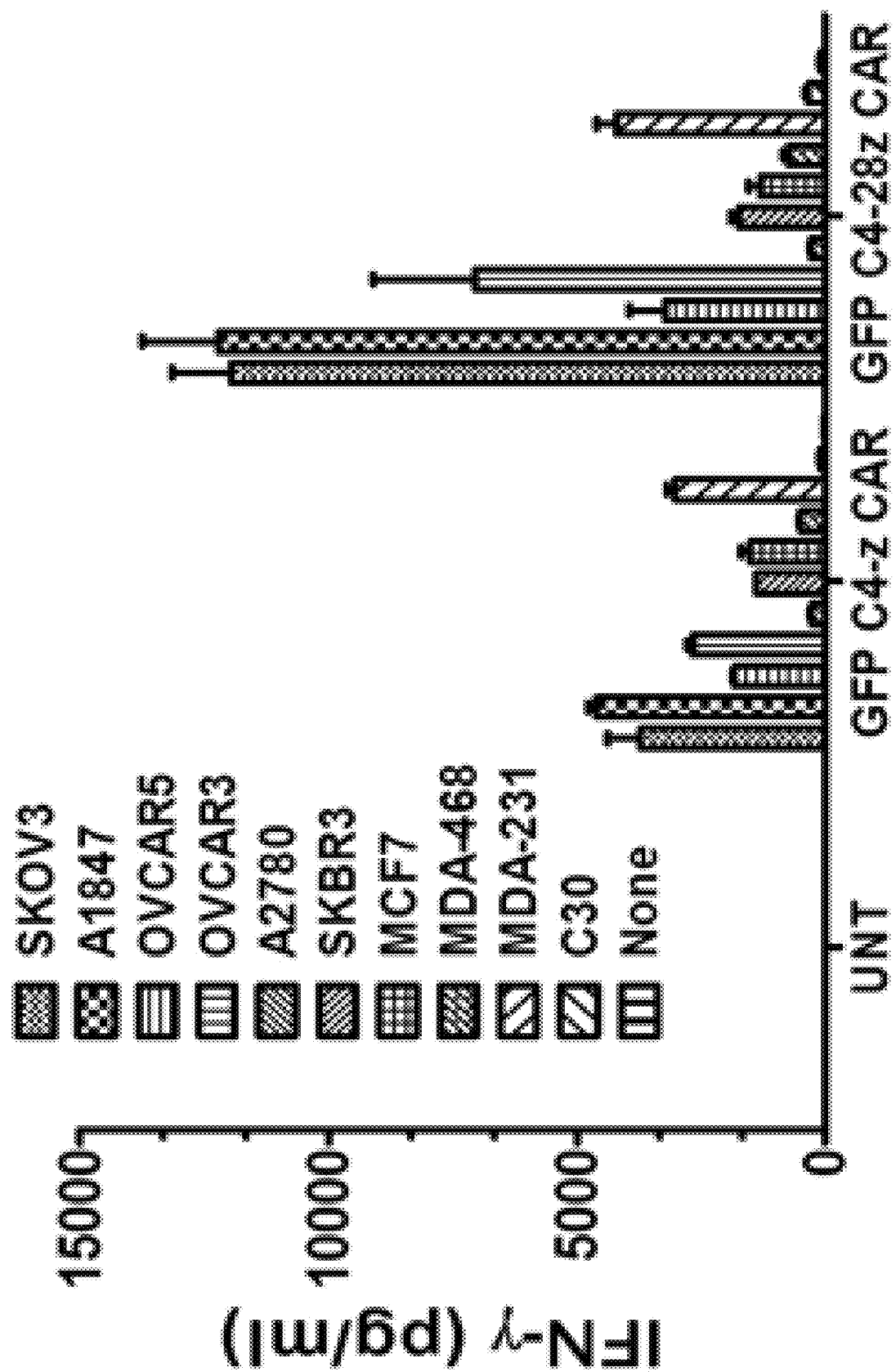
FIG. 3 is a graph depicting IFN-γ secretion by C4-z and C4-28z CAR-transduced T cells but not untransduced T cells (UNT), following overnight incubation with FRa(+) human cancer cell lines. Mean IFN-γ concentration±SEM (pg/mL) from triplicate cultures is shown.

To evaluate the impact of costimulation on antitumor function of CAR-T cells in vitro, engineered human T cells and cancer cells were co-cultured and T-cell reactivity measured by proinflammatory cytokine secretion. GFP C4-z or GFP C4-28z CAR-T cells recognized FRa+ (SKOV3, A1847, OVCAR3) ovarian and breast cancer lines (SKBR3, MCF7, MDA-231) and secreted high levels of IFN-γ, which was associated with the level of FRa expression by tumor cells but not when stimulated with FRa− cell lines (C30) (FIG. 3).

Figure 4:
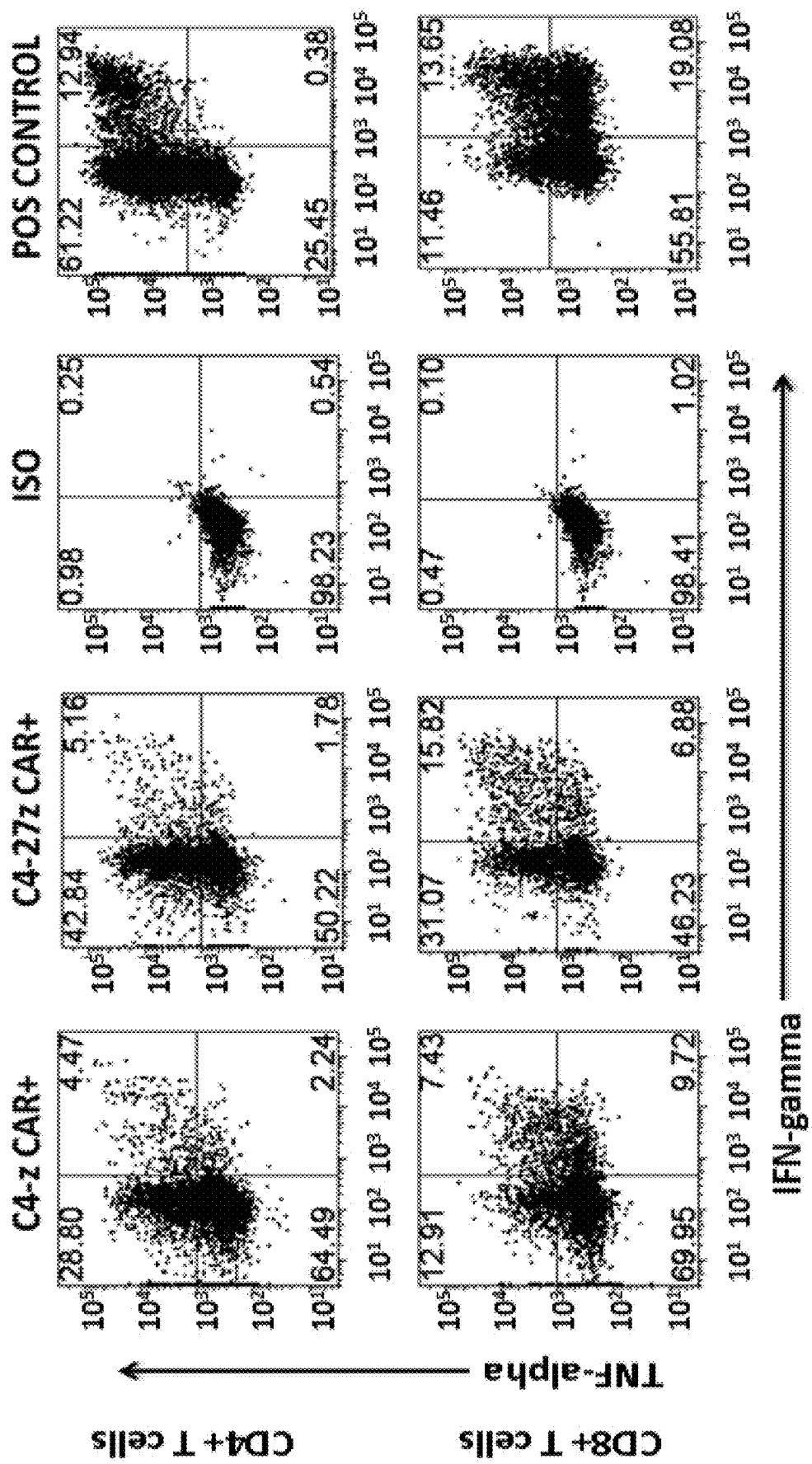
FIG. 4 is a series of graphs depicting IFN-γ and TNF-α expression analyzed by intracellular staining of C4-z and C4-27z CAR T cells after a 5-hour co-culture with FRa(+) ovarian cancer SKOV3 cells. PMA/Ionomycin stimulated T cells served as positive control.
Figure 5:
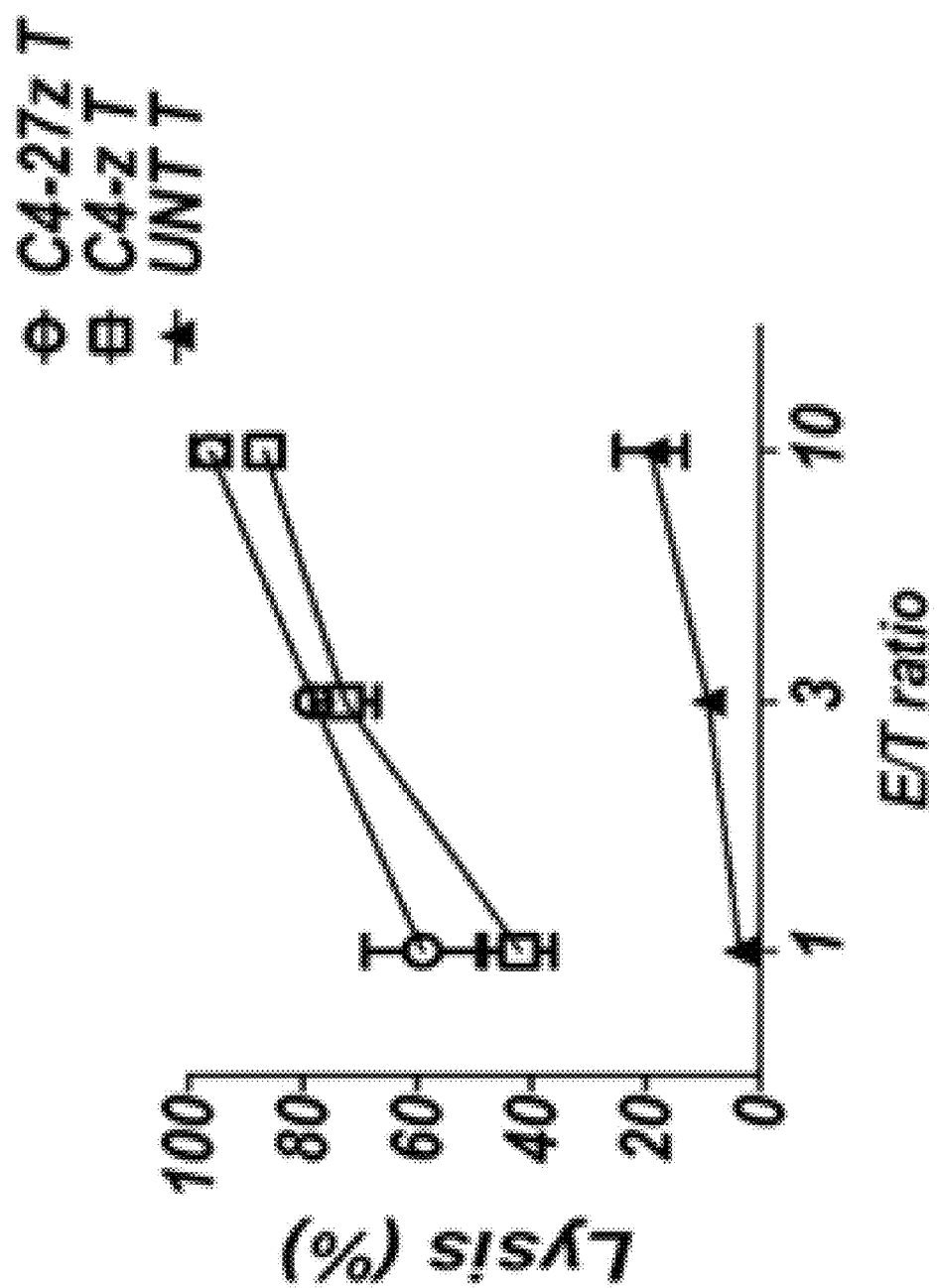
FIG. 5 is a graph depicting C4-z and C4-27z CAR T cell-mediated lysis of FRa(+) SKOV3 cells in overnight culture.

Moreover, the C4-27z CAR containing the CD27 costimulatory signaling domain also exert enhanced reactivity in an in vitro 5-hour IFN-γ and TNF-α intracellular staining assay. As shown in FIG. 4, after stimulation with FRa+ SKOV3 cells, a significant proportion of C4-z and C4-27z CAR+ T cells coexpressed IFN-γ and TNF-α. CAR expressing IFN-γ in response to SKOV3 were predominantly CD8+T cells, whereas CAR expressing TNF-α responding to SKOV3 were predominantly CD4+ T cells. Importantly, C4-27z CAR+ CD8+ T cells express more IFN-γ than C4-z CAR+ CD8+ T cells. Both C4-27z CAR+ CD4+ and CD8+ T cells express more TNF-α than C4-z CAR+ T cells (FIG. 4). The cytolytic potential of FRa-specific CAR-T cells was evaluated in vitro using overnight a luminescence co-culture assay. CAR-T cells were co-cultured with FRa+ cancer cells or FRa− C30 expressing firefly luciferase (fLuc+) and assessed for bioluminescence following overnight culture. Representative results showed that both FR-z and FR-27z CAR-T cells specifically eliminated FRa+ SKOV3 ovarian cancer cells (FIG. 5) but not FRa− C30 cells. Untransduced T cells did not lyse ovarian cancer cells (FIG. 5).

Figure 6A:
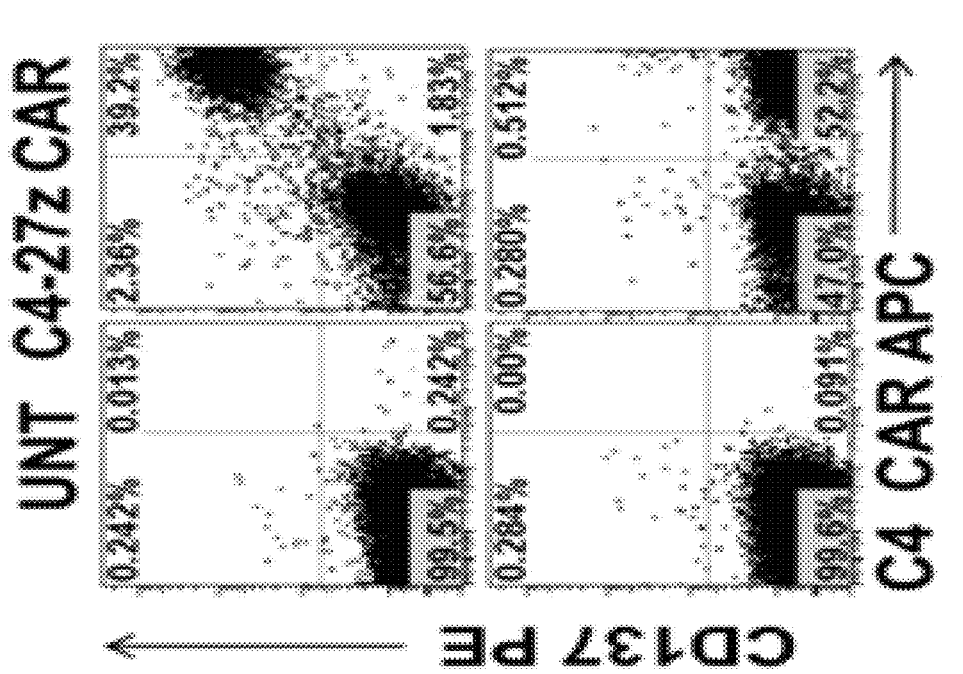
FIGS. 6A-6B are series of graphs depicting the detection of antigen-specific T-cell activation by the induction of CD137 expression.
Figure 6B:
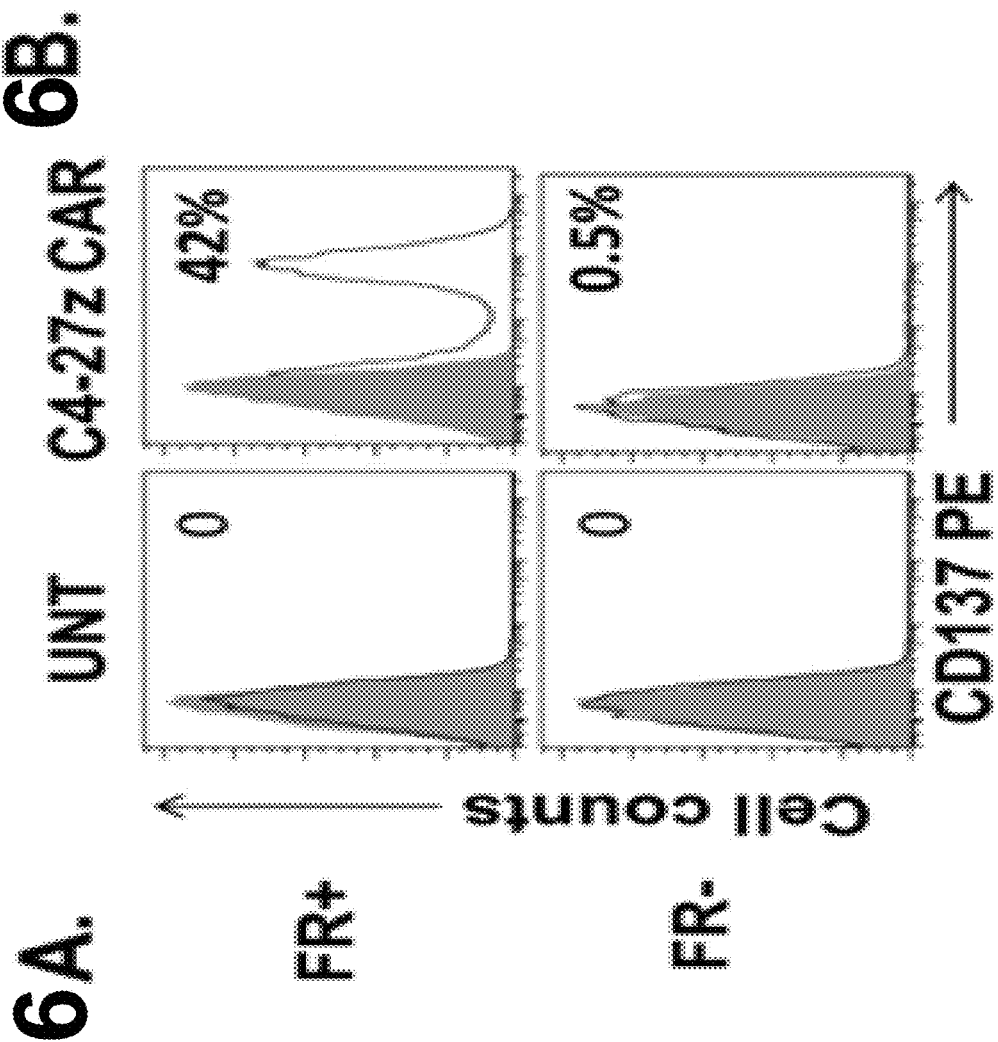

Previous studies have shown that CD137 is upregulated on CD8+ T cells after T-cell receptor stimulation. C4-27z T cells were incubated with both FRa+ and FRa− target cells and robust upregulation of CD137 was found when the cells were incubated with FRa+ tumor cells (FIG. 6A). CD137 up-regulation was restricted to the CAR+ T cells population, and although not wishing to be bound by any particular theory, this indicated its dependence on antigen specific stimulation (FIG. 6B).

Figures 7A, 7B:
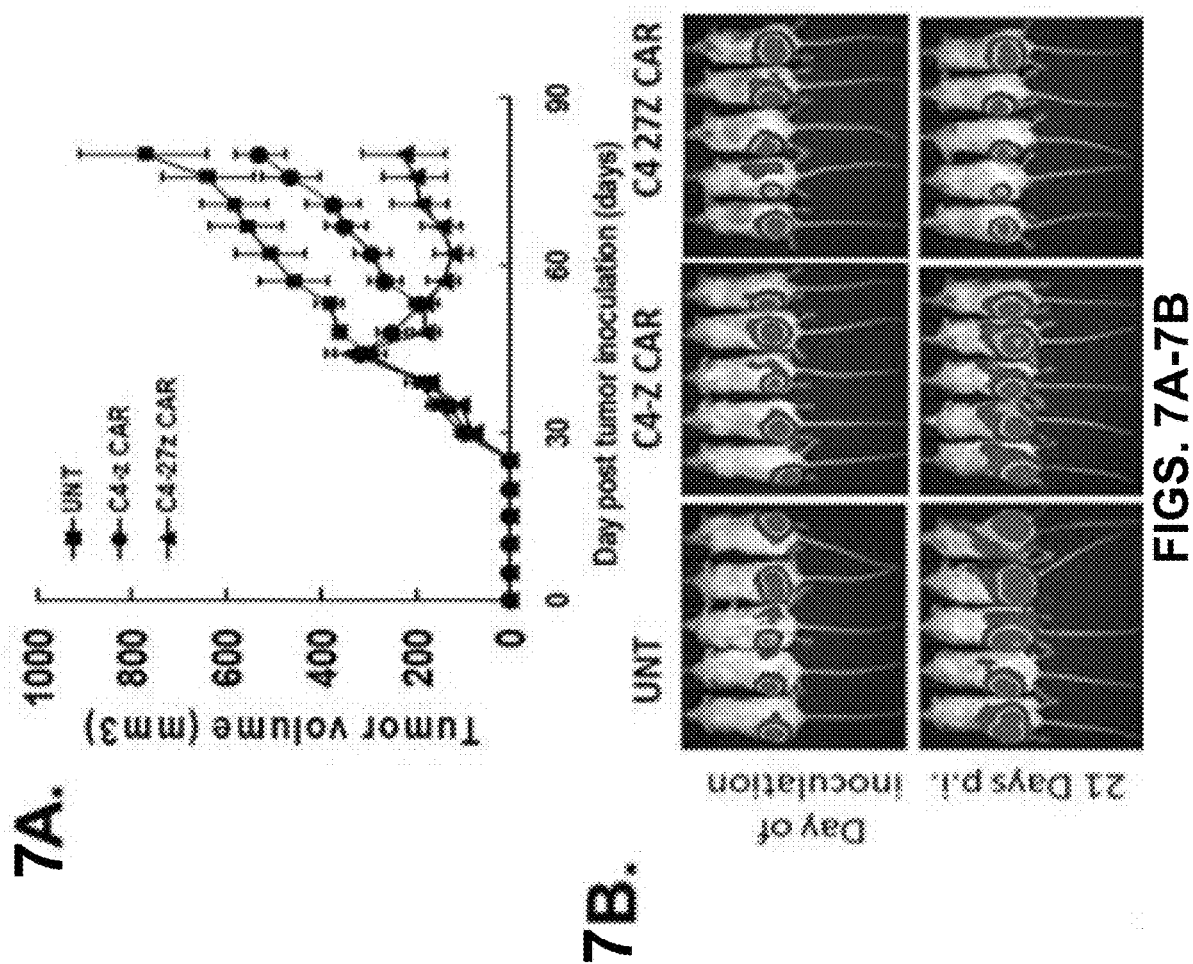
FIGS. 7A-7B are series of a graph and images depicting how costimulated C4 CAR T cells mediate regression of human ovarian cancer xenografts.

Costimulated C4 CAR T Cells Mediate Regression of Human Ovarian Cancer Xenografts The antitumor efficacy of C4 CAR constructs were evaluated in a xenograft model of large, established cancer. Immunodeficient NOD/SCID/IL-2Rgcnull (NSG) mice were inoculated subcutaneously (s.c.) with firefly luciferase (fLuc)-transfected FRa+ SKOV3 human ovarian cancer cells on the flank and received intravenous (i.v.) injections of CART cells on day 40 post-tumor inoculation (p.i.), when tumors were 250 mm³ or more in size. Tumors in mice receiving untransduced (UNT) T cell progressed beyond the time of T cell transfer as measured by caliper-based sizing and bioluminescence imaging (BLI; FIGS. 7A-7B). Tumor growth was modestly delayed in mice receiving C4-z T cells when compared with the UNT control group at the latest evaluated time point (45 days after T-cell injection). In contrast, mice receiving an i.v. injection of fully human C4-27z T cells experienced significant tumor regression. This tumor regression was significantly better than that observed in mice injected with C4-z T cells (p<0.01) (FIGS. 7A-7B).

Figure 8:
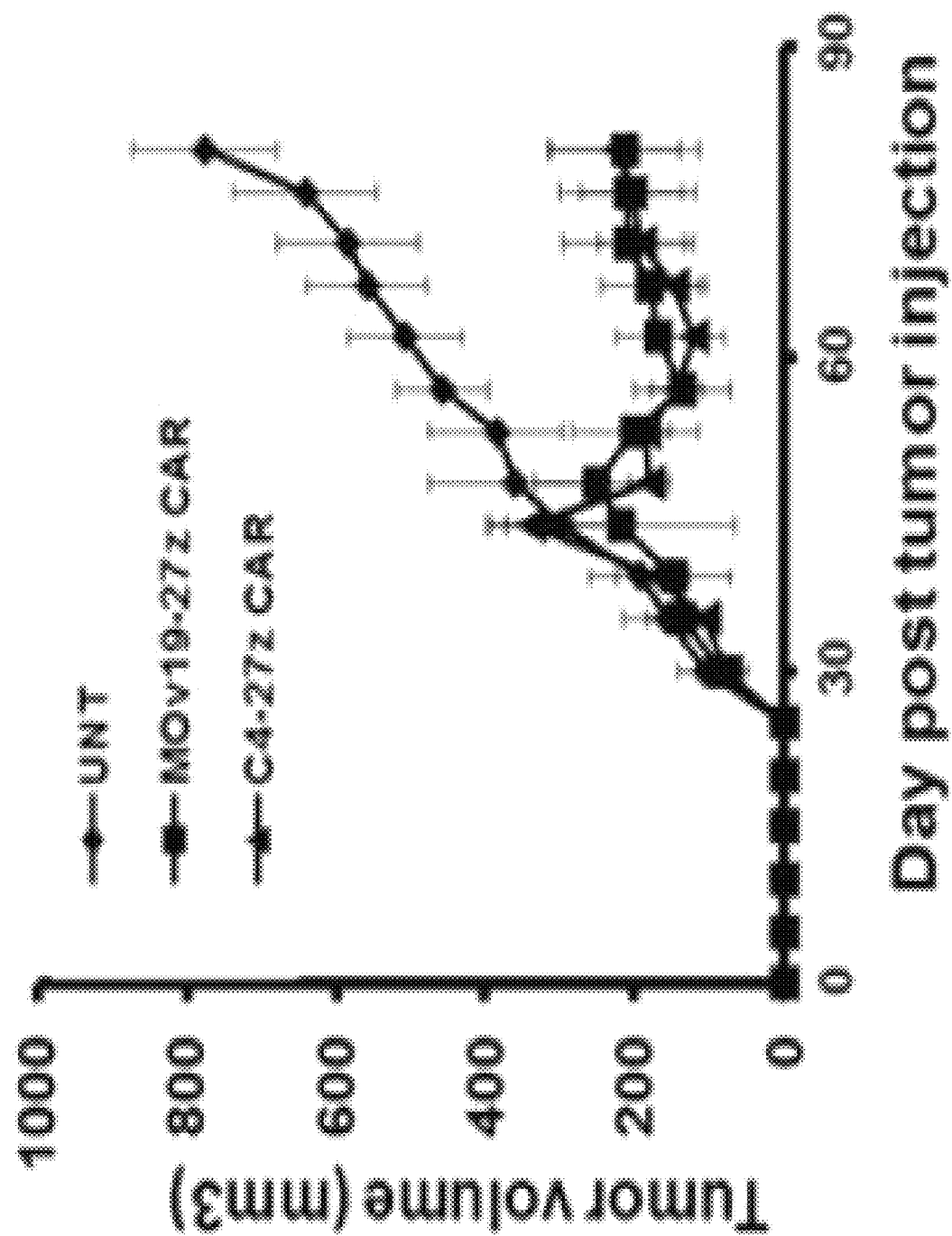
FIG. 8 is a graph depicting a comparison of antitumor activity of fully human C4 CAR and murine anti-human MOV19 CAR in vivo.

The novel fully human C4-27z CAR and murine antihuman MOV19-27z CAR were compared in vivo. Data (FIG. 8) showed that C4-27z CAR had slightly superior antitumor activity when compared with MOv19-27z CAR after T cell injection.

Example 2: CAR Sequences

C4-CD27CD3z-CAR (amino acid sequence)
(SEQ ID NO: 1)
MALPVTALLLPLALLLHAARPGSQLVESGGGLVQPGRSLRLSCTTSGFTF

GDYAMIWARQAPGKGLEWVSSISSSSSYIYYADSVKGRFTISRDNAKNSL

YLQMNSLRAEDTAVYYCARERYDFWSGMDVWGKGITVTVSSGGGGSGGGG

SGGGSAQSALTQPASVSGSPGQSITISCTGTSSDVGSYNLVSWYQQHPGKA

PKLMIYEGSKRPSGVSNRFSGSKSGNAASLTISGLQAEDEADYYCQSYDS

SLSVVFGGGTKLTVLGASTTTPAPRPPTPAPTIASQPLSLRPEACRPAAG

GAVHTRGLDFACDIYIWAPLAGTCGVLLLSLVITLYCQRRKYRSNKGESP

VEPAEPCRYSCPREEEGSTIPIQEDYRKPEPACSPRVKFSRSADAPAYKQ

GQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

C4-CD28CD3z-CAR (amino acid sequence)
(SEQ ID NO: 2)
MALPVTALLLPLALLLIIAARPGSQLVESGGGLVQPGRSLRLSCTTSGFT

FGDYAMIWARQAPGKGLEWVSSISSSSSYIYYADSVKGRFTISRDNAKNS

LYLQMNSLRAEDTAVYYCARERYDFWSGMDVWGKGTTVTVSSGGGGSGGG

GSGGGSAQSALTQPASVSGSPGQSITISCTGTSSDVGSYNLVSWYQQHPGK

APKLMIYEGSKRPSGVSNRFSGSKSGNAASLTISGLQAEDEADYYCQSYD

SSLSVVFGGGTKLTVLGASTTTPAPRPPTPAPTIASQPLSLRPEACRPAA

GGAVHTRGLDFACDFWVLVVVGGVLACYSLLVTVAFIIFWVRSKRSRLLH

SDYMNMTPRRPGPTRKHYQPYAPPRDFAAYRSIDRVKFSRSADAPAYKQG

QNQLYNELNLGRREEYDVLDKRRGRDPEMGGKPRRKNPQEGLYNELQKDK

MAEAYSEIGMKGERRRGKGHDGLYQGLSTATKDTYDALHMQALPPR

C4-CD3z-CAR (amino acid sequence)
(SEQ ID NO: 3)
MALPVTALLLPLALLLHAAKPGSQLVESGGGLVQPGRSLRLSCTTSGFT

FGDYAMIWARQAPGKGLEWVSSISSSSSYIYYADSVKGRFTISRDNAKN

SLYLQMNSLRAEDTAVYYCARERYDFWSGMDVWGKGTTVTVSSGGGGSG

GGGSGGGSAQSALTQPASVSGSPGQSITISCTGTSSDVGSYNLVSWYQQH

PGKAPKLMIYEGSKRPSGVSNRFSGSKSGNAASLTISGLQAEDEADYYC

QSYDSSLSVVFGGGTKLTVLGASTTTPAPRPPTPAPTIASQPLSLRPEAC

RPAAGGAVHTRGLDFACDIYIWAPLAGTCGVLLLSLVITLYCRVKFSRS

ADAPAYKQGQNQLYNELNLGRREEYDVLDKRRGRDPEMGGKPRRKNPQE

GLYNELQKDKMAEAYSEIGMKGERRRGKGHDGLYQGLSTATKDTYDALH
MQALPPR

CD8a leader (amino acid sequence)
(SEQ ID NO: 4)
MALPVTALLLPLALLLHAARP

C4 scFv (amino acid sequence)
(SEQ ID NO: 5)
QLVESGGGLVQPGRSLRLSCTTSGFTFGDYAMIWARQAPGKGLEWVSSIS
SSSSYIYYADSVKGRITISRDNAKNSLYLQMNSLRAEDTAVYYCARERYD
FWSGMDVWGKGTTVTVSSGGGGSGGGGSGGSAQSALTQPASVSGSPGQSI
TISCTGTSSDVGSYNLVSWYQQHPGKAPKLMIYEGSKRPSGVSNRFSGSK
SGNAASLTISGLQAEDEADYYCQSYDSSLSVVFGGGTKLTVLG CD8a hinge (amino acid sequence)
(SEQ ID NO: 6)
TTTPAPRPPTPAPTIASQPLSLRPEACRPAAGGAVHTRGLDFACD CD8a transmembrane (amino acid sequence)
(SEQ ID NO: 7)
IYIWAPLAGTCGVLLLSLVITLYC CD28 transmembrane (amino acid sequence)
(SEQ ID NO: 8)
FWVLVVVGGVLACYSLLVTVAFIIFWV CD27 Intracellular domain (amino acid sequence)
(SEQ ID NO: 9)
QRRKYRSNKGESPVEPAEPCRYSCPREEEGSTIPIQEDYRKPEPACSP CD28 Intracellular domain (amino acid sequence)
(SEQ ID NO: 10)
RSKRSRLLHSDYMNMTPRRPGPTRKHYQPYAPPRDFAAYRS CD3 zeta (amino acid sequence)
(SEQ ID NO: 11)
RVKFSRSADAPAYKQGQNQLYNELNLGRREEY**DVLDKRRGRDPEMGGKPR
RKNPQEGLYNELQKDKMAEAYSEIGMKGERRRGKGHDGLYQGLSTATKDT
YDALHMQALPPR**

C4-CD27CD3z-CAR (nucleotide sequence)
(SEQ ID NO: 12)
**ATGGCCTTACCAGTGACCGCCTTGCTCCTGCCGCTGGCCTTGCTGCTCC
ACGCCGCCAGGCCGGGATCCC**AGCTGGTGGAGTCTGGGGGAGGCTTGGT
ACAGCCAGGGCGGTCCCTGAGACTCTCCTGCACAACTTCTGGATTCACT
TTTGGTGATTATGCTATGATCTGGGCCCGCCAGGCTCCAGGGAAGGGGC
TGGAGTGGGTCTCATCCATTAGTAGTAGTAGTTACATATACTACGC
AGACTCAGTGAAGGGCCGATTCACCATCTCCAGAGACAACGCCAAGAAC
TCACTGTATCTGCAAATGAACAGCCTGAGAGCCGAGGACACGGCTGTGT
ATTACTGTGCGAGAGAACGATACGATTTTTGGAGTGGAATGGACGTCTG
GGGCAAAGGGACCACGGTCACCGTCTCGAGTGGTGGAGGCGGTTCAGGC
GGAGGTGGCTCTGGCGGTAGTGCACAGTCTGCCCTGACTCAGCCTGCCT
CCGTGTCTGGGTCTCCTGGACAGTCGATCACCATCTCCTGCACTGGAAC
CAGCAGTGATGTTGGGAGTTATAACCTTGTCTCCTGGTACCAACAGCAC
CCAGGCAAAGCCCCCAAACTCATGATTTATGAGGGCAGTAAGCGGCCCT
CAGGGGTTTCTAATCGCTTCTCTGGCTCCAAGTCTGGCAACGCGGCCTC
CCTGACAATCTCTGGGCTCCAGGCTGAGGACGAGGCTGATTATTACTGC
CAGTCCTATGACAGCAGCCTGAGTGTGGTATTCGGCGGAGGGACCAAGC
TGACCGTCCTAGGTGCTAGCACCACGACGCCAGCGCCGCGACCACCAAC
ACCGGCGCCCACCATCGCGTCGCAGCCCCTGTCCCTGCGCCCAGAGGCG
TGCCGGCCAGCGGCGGGGGGCGCAGTGCACACGAGGGGGCTGGACTTC
GCCTGTGATATCTACATCTGGGCGCCCTTGGCCGGGACTTGTGGGGTCC TTCTCCTGTCACTGGTTATCACCCTTTACTGCCAACGAAGGAAATATAG
ATCAAACAAAGGAGAAAGTCCTGTGGAGCCTGCAGAGCCTTGTCGTTAC
AGCTGCCCCAGGGAGGAGGAGGGCAGCACCATCCCCATCCAGGAGGATT
ACCGAAAACCGGAGCCTGCCTGCTCCCCC**AGAGTGAAGTTCAGCAGGAG
CGCAGACGCCCCCGCGTACAAGCAGGGCCAGAACCAGCTCTATAACGAG
CTCAATCTAGGACGAAGAGAGGAGTACGATGTTTTGGACAAGACACGTG
GCCGGGACCCTGAGATGGGGGGAAAGCCGAGAAGGAAGAACCCTCAGG
AAGGCCTGTACAATGAACTGCAGAAAGATAAGATGGCGGAGGCCTACAG
TGAGATTGGGATGAAAGGCGAGCGCCGGAGGGGCAAGGGGCACGATGG
CCTTTACCAGGGTCTCAGTACAGCCACCAAGGACACCTACGACGCCCTT
CACATGCAGGCCCTGCCCCCTCGCTAA**

C4-CD28CD3z-CAR (nucleotide sequence)
(SEQ ID NO: 13)
**ATGGCCTTACCAGTGACCGCCTTGCTCCTGCCGCTGGCCTTGCTGCTCC
ACGCCGCCAGGCCG**GGATCCCAGCTGGTGGAGTCTGGGGGAGGCTTGGTA
CAGCCAGGGCGGTCCCTGAGACTCTCCTGCACAACTTCTGGATTCACTTT
TGGTGATTATGCTATGATCTGGGCCCGCCAGGCTCCAGGGAAGGGGCTGG
AGTGGGTCTCATCCATTAGTAGTAGTAGTTACATATACTACGCAGAC
TCAGTGAAGGGCCGATTCACCATCTCCAGAGACAACGCCAAGAACTCAC
TGTATCTGCAAATGAACAGCCTGAGAGCCGAGGACACGGCTGTGTATTA
CTGTGCGAGAGAACGATACGATTTTTGGAGTGGAATGGACGTCTGGGGC
AAAGGGACCACGGTCACCGTCTCGAGTGGTGGAGGCGGTTCAGGCGGA
GGTGGCTCTGGCGGTAGTGCACAGTCTGCCCTGACTCAGCCTGCCTCCG
TGTCTGGGTCTCCTGGACAGTCGATCACCATCTCCTGCACTGGAACCAG
CAGTGATGTTGGGAGTTATAACCTTGTCTCCTGGTACCAACAGCACCCA
GGCAAAGCCCCCAAACTCATGATTTATGAGGGCAGTAAGCGGCCCTCAG
GGGTTTCTAATCGCTTCTCTGGCTCCAAGTCTGGCAACGCGGCCTCCCT
GACAATCTCTGGGCTCCAGGCTGAGGACGAGGCTGATTATTACTGCCAG
TCCTATGACAGCAGCCTGAGTGTGGTATTCGGCGGAGGGACCAAGCTGA
CCGTCCTAGGTGCTAGCACCACGACGCCAGCGCCGCGACCACCAACACC
GGCGCCCACCATCGCGTCGCAGCCCCTGTCCCTGCGCCCAGAGGCGTGC
CGGCCAGCGGCGGGGGGCGCAGTGCACACGAGGGGGCTGGACTTCGCC
TGTGA**TTTTTGGGTGCTGGTGGTGGTTGGTGGAGTCCTGGCTTGCTATA
GCTTGCTAGTAACAGTGGCCTTTATTATTTTCTGGGTG**AGGAGTAAGAG
GAGCAGGCTCCTGCACAGTGACTACATGAACATGACTCCCCGCCGCCCC
GGGCCCACCCGCAAGCATTACCAGCCCTATGCCCCACCACGCGACTTCG
CAGCCTATCGCTCC**ATCGATAGAGTGAAGTTCAGCAGGAGCGCAGACGC
CCCCGCGTACCAGCAGGGCCAGAACCAGCTCTATAACGAGCTCAATCTA
GGACGAAGAGAGGAGTACGATGTTTTGGACAAGAGACGTGGCCGGGAC
CCTGAGATGGGGGGAAAGCCGAGAAGGAAGAACCCTCAGGAAGGCCTG
TACAATGAACTGCAGAAAGATAAGATGGCGGAGGCCTACAGTGAGATTG
GGATGAAAGGCGAGCGCCGGAGGGGCAAGGGGCACGATGGCCTTTACC**

AGGGTCTCAGTACAGCCACCAAGGACACCTACGACGCCCTTCACATGCA

GGCCCTGCCCCCTCGCTAA

C4-CD3z-CAR (nucleotide sequence)
(SEQ ID NO: 14)
ATGGCCTTACCAGTGACCGCCTTGCTCCTGCCGCTGGCCTTGCTGCTCC

ACGCCGCCAGGCCGGGATCCCAGCTGGTGGAGTCTGGGGGAGGCTTGGT

ACAGCCAGGGCGGTCCCTGAGACTCTCCTGCACAACTTCTGGATTCACT

TTTGGTGATTATGCTATGATCTGGGCCCGCCAGGCTCCAGGGAAGGGGC

TGGAGTGGGTCTCATCCATTAGTAGTAGTAGTAGTTACATATACTACGCA

GACTCAGTGAAGGGCCGATTCACCATCTCCAGAGACAACGCCAAGAACT

CACTGTATCTGCAAATGAACAGCCTGAGAGCCGAGGACACGGCTGTGTA

TTACTGTGCGAGAGAACGATACGATTTTTGGAGTGGAATGGACGTCTGG

GGCAAAGGGACCACGGTCACCGTCTCGAGTGGTGGAGGCGGTTCAGGC

GGAGGTGGCTCTGGCGGTAGTGCACAGTCTGCCCTGACTCAGCCTGCCT

CCGTGTCTGGGTCTCCTGGACAGTCGATCACCATCTCCTGCACTGGAAC

CAGCAGTGATGTTGGGAGTTATAACCTTGTCTCCTGGTACCAACAGCAC

CCAGGCAAAGCCCCCAAACTCATGATTTATGAGGGCAGTAAGCGGCCCT

CAGGGGTTTCTAATCGCTTCTCTGGCTCCAAGTCTGGCAACGCGGCCTC

CCTGACAATCTCTGGGCTCCAGGCTGAGGACGAGGCTGATTATTACTGC

CAGTCCTATGACAGCAGCCTGAGTGTGGTATTCGGCGGAGGGACCAAGC

TGACCGTCCTAGGTGCTAGCACCACGACGCCAGCGCCGCGACCACCAAC

ACCGGCGCCCACCATCGCGTCGCAGCCCCTGTCCCTGCGCCCAGAGGCG

TGCCGGCCAGCGGCGGGGGCGCAGTGCACACGAGGGGGCTGGACTTC

GCCTGTGATATCTACATCTGGGCGCCCTTGGCCGGGACTTGTGGGGTCC

TTCTCCTGTCACTGGTTATCACCCTTTACTGCAGAGTGAAGTTCAGCAGG

AGCGCAGACGCCCCCGCGTACAAGCAGGGCCAGAACCAGCTCTATAACG

AGCTCAATCTAGGACGAAGAGAGGAGTACGATGTTTTGGACAAGAGACG

TGGCCGGGACCCTGAGATGGGGGGAAAGCCGAGAAGGAAGAACCCTCA

GGAAGGCCTGTACAATGAACTGCAGAAAGATAAGATGGCGGAGGCCTAC

AGTGAGATTGGGATGAAAGGCGAGCGCCGAGGGGCAAGGGGCACGAT

GGCCTTTACCAGGGTCTCAGTACAGCCACCAAGGACACCTACGACGCCC

TTCACATGCAGGCCCTGCCCCCTCGCTAA

CD8a leader (nucleotide sequence)
(SEQ ID NO: 15)
ATGGCCTTACCAGTGACCGCCTTGCTCCTGCCGCTGGCCTTGCTGCTCC
ACGCCGCCAGGCCG C4 scFv (nucleotide sequence)
(SEQ ID NO: 16)
CAGCTGGTGGAGTCTGGGGGAGGCTTGGTACAGCCAGGGCGGTCCCTG

AGACTCTCCTGCACAACTTCTGGATTCACTTTTGGTGATTATGCTATGAT

CTGGGCCCGCCAGGCTCCAGGGAAGGGGCTGGAGTGGGTCTCATCCATT

AGTAGTAGTAGTAGTTACATATACTACGCAGACTCAGTGAAGGGCCGAT

TCACCATCTCCAGAGACAACGCCAAGAACTCACTGTATCTGCAAATGAA

CAGCCTGAGAGCCGAGGACACGGCTGTGTATTACTGTGCGAGAGAACGA

TACGATTTTTGGAGTGGAATGGACGTCTGGGGCAAAGGGACCACGGTCA

CCGTCTCGAGTGGTGGAGGCGGTTCAGGCGGAGGTGGCTCTGGCGGTA

GTGCACAGTCTGCCCTGACTCAGCCTGCCTCCGTGTCTGGGTCTCCTGG

ACAGTCGATCACCATCTCCTGCACTGGAACCAGCAGTGATGTTGGGAGT

TATAACCTTGTCTCCTGGTACCAACAGCACCCAGGCAAAGCCCCCAAAC

TCATGATTTATGAGGGCAGTAAGCGGCCCTCAGGGGTTTCTAATCGCTT

CTCTGGCTCCAAGTCTGGCAACGCGGCCTCCCTGACAATCTCTGGGCTC

CAGGCTGAGGACGAGGCTGATTATTACTGCCAGTCCTATGACAGCAGCC

TGAGTGTGGTATTCGGCGGAGGGACCAAGCTGACCGTCCTAGGT

CD8a hinge (nucleotide sequence)
(SEQ ID NO: 17)
ACCACGACGCCAGCGCCGCGACCACCAACACCGGCGCCCACCATCGCGT
CGCAGCCCCTGTCCCTGCGCCCAGAGGCGTGCCGGCCAGCGGCGGGGG
GCGCAGTGCACACGAGGGGGCTGGACTTCGCCTGTGAT CD8a transmembrane (nucleotide sequence)
(SEQ ID NO: 18)
ATCTACATCTGGGCGCCCTTGGCCGGGACTTGTGGGGTCCTTCTCCTGT
CACTGGTTATCACCCTTTACTGC CD28 transmembrane (nucleotide sequence)
(SEQ ID NO: 19)
TTTTGGGTGCTGGTGGTGGTTGGTGGAGTCCTGGCTTGCTATAGCTTGC
TAGTAACAGTGGCCTTTATTATTTTCTGGGTG CD27 Intracellular domain (nucleotide sequence)
(SEQ ID NO: 20)
CAACGAAGGAAATATAGATCAAACAAAGGAGAAAGTCCTGTGGAGCCTG
CAGAGCCTTGTCGTTACAGCTGCCCCAGGGAGGAGGAGGGCAGCACCAT
CCCCATCCAGGAGGATTACCGAAAACCGGAGCCTGCCTGCTCCCCC CD28 Intracellular domain (nucleotide sequence)
(SEQ ID NO: 21)
AGGAGTAAGAGGAGCAGGCTCCTGCACAGTGACTACATGAACATGACTC
CCCGCCGCCCCGGGCCCACCCGCAAGCATTACCAGCCCTATGCCCCACC
ACGCGACTTCGCAGCCTATCGCTCC CD3 zeta (nucleotide sequence)
(SEQ ID NO: 22)
AGAGTGAAGTTCAGCAGGAGCGCAGACGCCCCCGCGTACAAGCAGGGC

CAGAACCAGCTCTATAACGAGCTCAATCTAGGACGAAGAGAGGAGTACG

ATGTTTTGGACAAGAGACGTGGCCGGGACCCTGAGATGGGGGGAAAGC

CGAGAAGGAAGAACCCTCAGGAAGGCCTGTACAATGAACTGCAGAAAGA

TAAGATGGCGGAGGCCTACAGTGAGATTGGGATGAAAGGCGAGCGCCG

GAGGGGCAAGGGGCACGATGGCCTTTACCAGGGTCTCAGTACAGCCACC

AAGGACACCTACGACGCCCTTCACATGCAGGCCCTGCCCCCTCGCTAA

Example 3: Additional Experiments Expressing PDA-C4-27Z RNA in Cells

Construction of In Vitro Transcription (IVT) Vectors and RNA Electroporation TO HERE A lentiviral vector encoding MOv19 anti-FR scFV coupled with a cytosolic tail comprised of a CD27 costimulatory domain had been engineered previously (Song et al. 2011. Cancer Res. July 1; 71(13):4617-27; Song et al. 2012 Jan. 19; 119(3):696-706). A novel, fully human scFV against the FR alpha (C4) was provided by Dr. Mari Figini from the Istituto Tumori Milano (Figini et al. 1998. Cancer Res. 991-996). MOv19 was removed and C4 scFV "swapped" to create a fully human CAR construct. After digestion, this construct was subcloned into a pD-A.lenti cloning site.2bg.150A vector (PDA) that has been optimized for T cell transduction and CAR expression (Zhao et al. 2010. *Microenvironment & Immunology.* 9053-9061). After specific restriction sites were added and the product amplified by PCR, the same approach was used to subclone CD19-27Z into PDA.

The C4 and CD19 CAR cDNAs were confirmed by direct sequencing and linearized by SpeI digestion prior to RNA IVT. The T7 mScript Standard mRNA Production System (Cellscript, Inc., Madison, Wis.) was used to generate capped/tailed IVT RNA. The IVT RNA was purified by phenol-chloroform extraction followed by RNeasy Mini Kit (Qiagen, Inc., Valencia, Calif.). Purified RNA was eluted in RNase-free water at 1-2 mg/ml and immediately stored at −80 C until use. RNA integrity was confirmed by 260/280 absorbance and visual confirmation on an RNA denaturing gel.

T Cells

Primary human T cells ($10^7$ cells) were isolated from healthy volunteer donors after leukapheresis and purchased from the Human Immunology Core at the University of Pennsylvania. T cells were cultured in complete media (RMPI 1640 supplemented with 10% heat-inactivated FBS, 100 U/mL penicillin, 100 ug/mL streptomycin sulfate, 10 mM HEPES) and stimulated with anti-CD3 and anti-CD28 mAbs-coated beads as described (Levine et al. 1997. *J. Immunology.* 5921-30). Human recombinant IL-2 (Novartis) was added one day after CD3/CD8 stimulation, then every other day at a 50 IU/mL final concentration, for 7-10 days, until T cell number reached approximately $1-3\times10^8$ cells. The stimulated T cells were washed twice with Opti-Mem at a final concentration on $10^8$/mL prior to electroporation. Subsequently, T cells were mixed with 10 ug/0.1 mL T cells of IVT RNA and electroporated in a 2-mm cuvette (Biorad) using an ECM830 Electro Square Wave Porator (Harvard Apparatus, BTX, Hollison, Mass.) at 500V, 700 usec, 1 pulse. Viability post transfection ranged from 50-80%. In all cases, viable T cells for experiments had 95-100% CAR expression at the time of use.

Flow Cytometric Analysis

Figure 10:
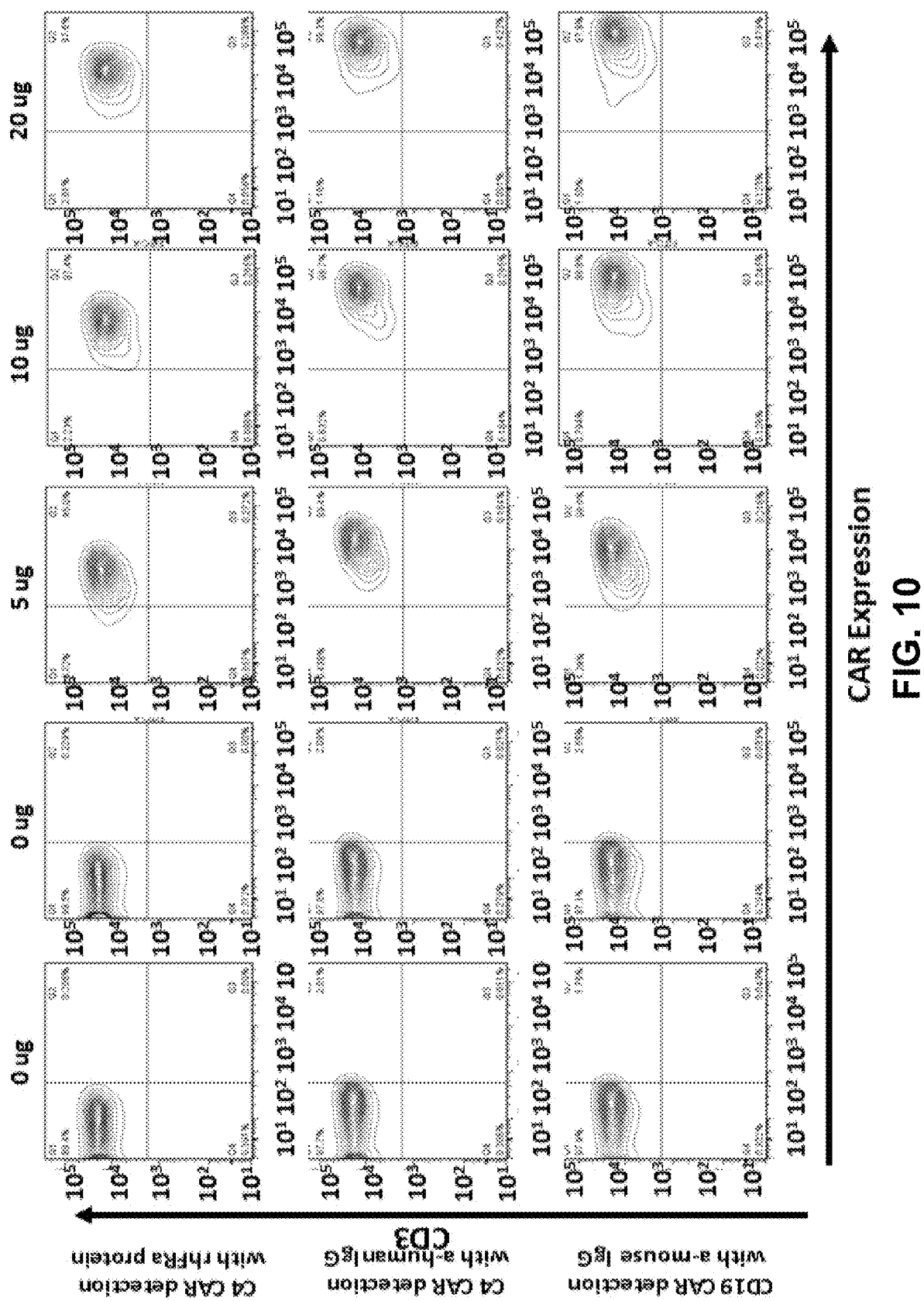
FIG. 10 illustrates representative data associated with experiments conducted to give rise to the data in FIGS. 9A-9B.

The following mAbs were used for phenotypic analysis and generation of the data shown in FIGS. 9A-9B and 10: i) Biotin-SP-conjugated AffiniPure Rabbit Anti-Human IgG (H+L), ii) Biotin-SP-conjugated AffiniPure Rabbit Anti-Mouse IgG (H+L) (Jackson, West Grove, Pa.), iii) Biotin-conjugated Recombinant Human FOLR1 (RD Systems, Minneapolis, Minn./Thermo Scientific, Rockford, Ill.), i.v) Strepavidin-APC (BD, San Jose, Calif.), v. BD ViaProbe (7-AAD). Briefly, $5\times10^5$ T cells electroporated with 5, 10 or 20 ug CD4 or CD19 RNA were labeled with either i), ii) (C4) or iii) (CD19). Subsequently, iv) was added to all samples, followed by wash 3× in FACS buffer (1×PBS, 2% FBS) and addition of v) for 10 minutes. Samples were analyzed on BD FACS Canto.

In the experiments shown in FIGS. 9A-9B, it was established that C4 experimental and CD19 control CARs are fully expressed by human T cells after electroporation with PDA-C4-27Z and PDA-CD19-27Z IVT RNA. In FIG. 9A, PDA-C4-27Z and PDA-CD19-27Z CAR expression was >95% and stable for up to 3 days after RNA electroporation with the ECM830 Electro Square Wave Porator (Harvard Apparatus, BTX, Hollison, Mass.) (500V, 700 usec, 1 pulse)]. Expression of C4 and CD19 declined significantly by day 5, suggestive of a considerable, though finite therapeutic window for RNA-based CAR activity. In FIG. 9B, it is demonstrated that the vast majority of electroporated T-cells are viable and functional 12 hrs after RNA electroporation, evidenced by robust translation of C4/CD19 and 7-AAD (BD ViaProbe) exclusion. Representative data associated with these experiments are depicted in FIG. 10.

Figure 11A:
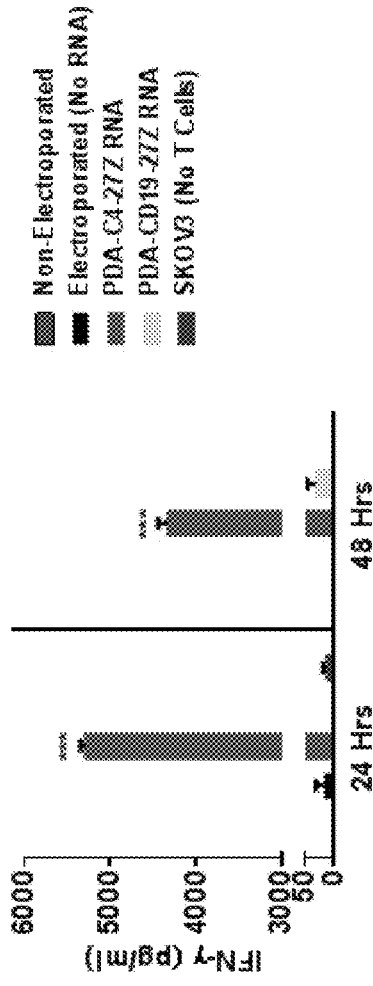
FIGS. 11A-11B are series of graphs illustrating that human T cells electroporated with PDA-C4-27Z RNA to express CAR mediate potent and selective immune response against aFR(+) expressing tumor cells. T cells expressing either PDA-C4-27Z or PDA-CD19-27Z RNA construct were co-cultured with a) αFR⁺ SKOV3-luciferase (FIG. 11A) orb) αFR⁻ C30-luciferase (FIG. 11B) cells at 1:1 ($10^5$:$10^5$ cells).
Figure 11B:
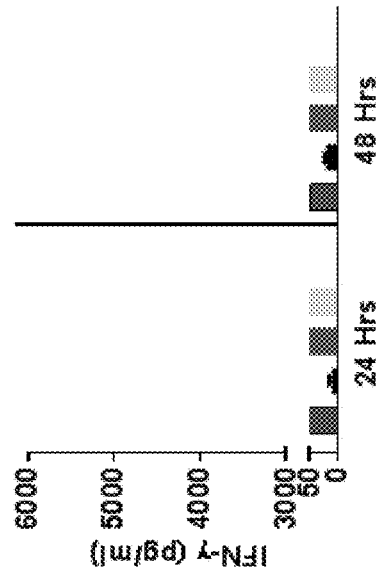

In FIGS. 11A-11B, data are presented that establish that human T cells electroporated with PDA-C4-27Z RNA to express CAR mediate a potent and selective immune response against αFR⁺ expressing tumor cells. Essentially, bug PDA-C4-27Z or PDA-CD19-27Z RNA was electroporated into T cells. One day later, T cells expressing either construct were co-cultured with a) αFR⁺ SKOV3-luciferase or b) αFR⁻ C30-luciferase cells at 1:1 ($10^5$:$10^5$ cells). Both non-electroporated T cells and electroporated T cells receiving no RNA served as controls. 24-48 hrs after co-culture, IFN-γ from cell-free supernatants was measured via ELISA. Values represent mean+/−SEM, n=3 per group, student t-test, ***p<0.001.

Figure 12:
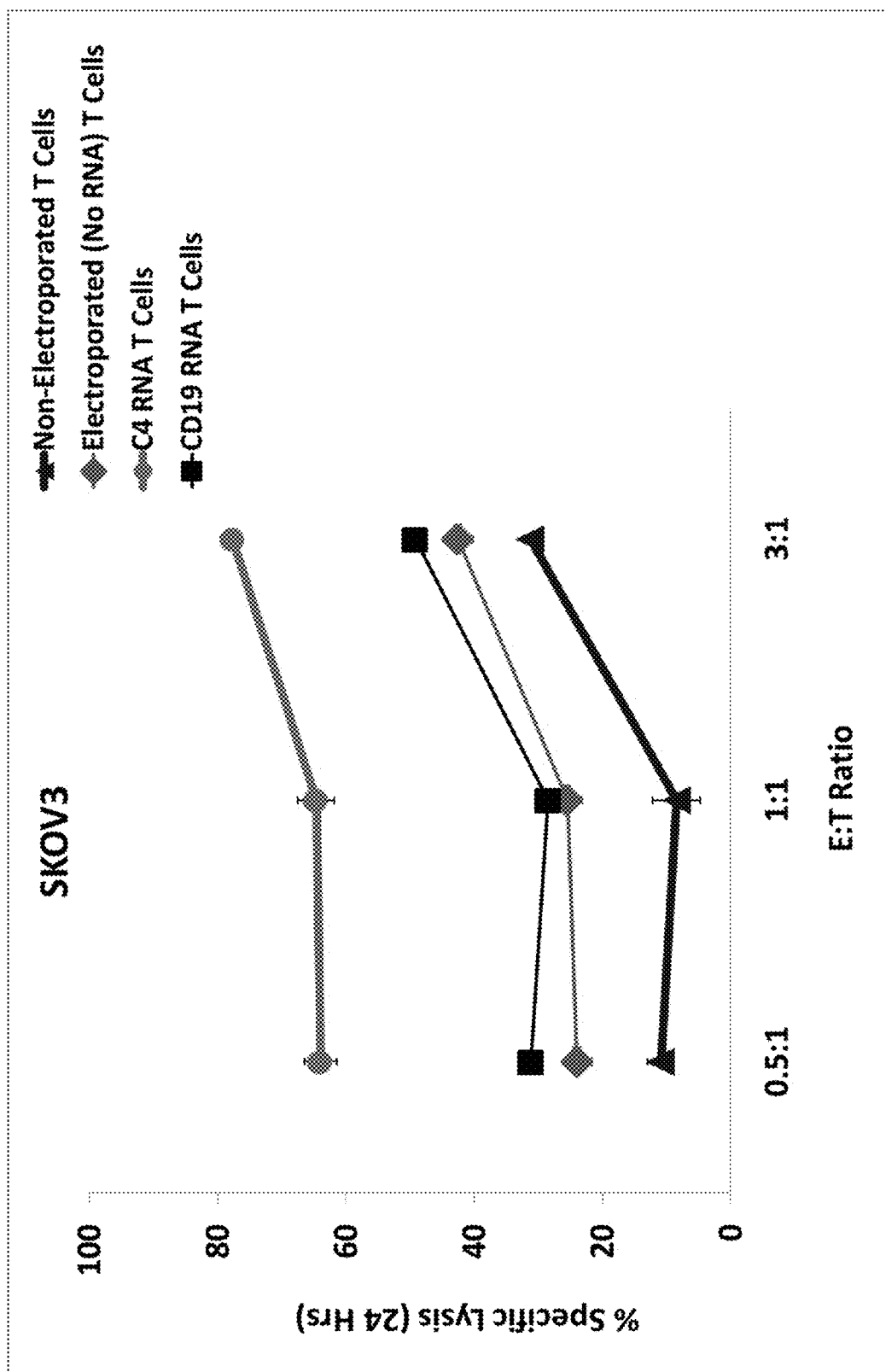
FIG. 12 is a graph illustrating that T cells electroporated with PDA-C4-27Z RNA to express CAR mediate vigorous cytolytic activity against aFR(+) expressing tumors.

In FIG. 12, data are shown that establish that human T cells electroporated with PDA-C4-27Z RNA to express CAR mediate vigorous cytolytic activity against αFR⁺ expressing tumors. Briefly, bug PDA-C4-27Z or PDA-CD19-27Z RNA was electroporated into T cells. 24 hrs later, T cells expressing each construct were co-cultured with αFR⁺ SKOV3-luciferase at different E:Ts as shown ($2.5\times10^4$-$1.5\times10^5$ E: $5\times10^4$ T). As in FIGS. 11A-11B, non-electroporated and electroporated T cells (no RNA) served as controls. Cell-based bioluminescence of cytolysis (detection of Firefly luciferase) was carried out per manufacturer's instructions (Applied Biosystems, Bedford, Mass.). Cytolytic activity is reported as % specific lysis +/−SEM, n=3-6 per group.

Figure 13A:
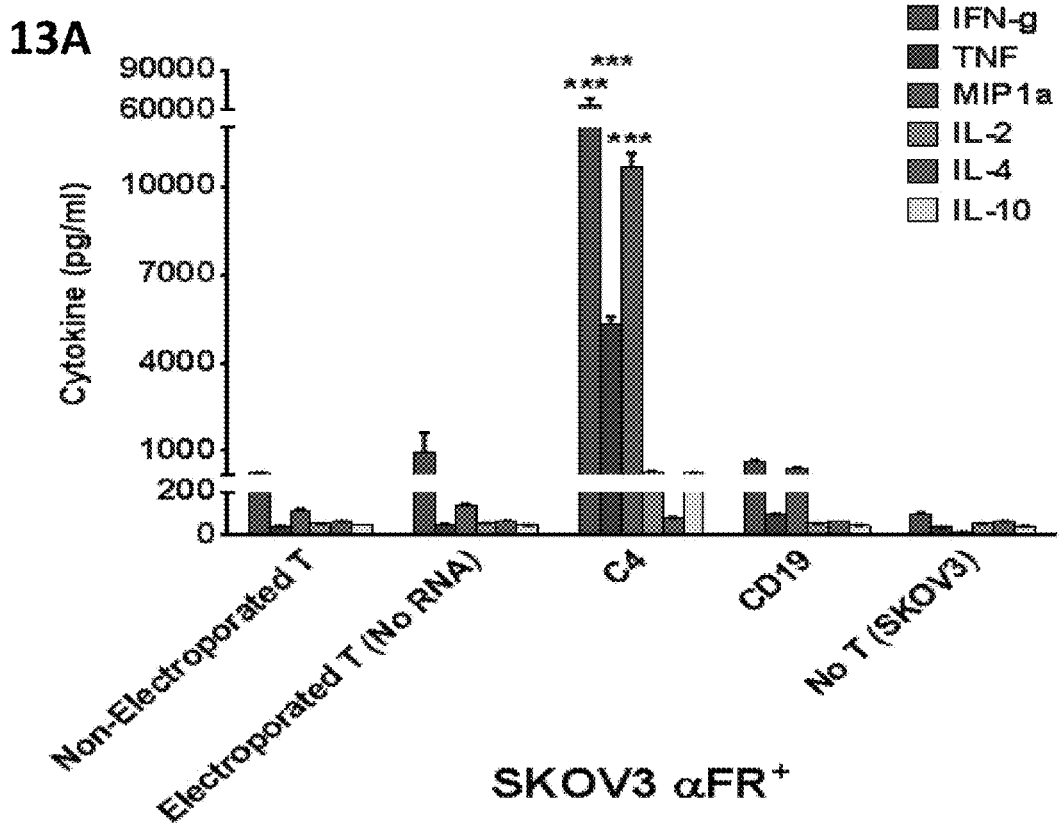
FIGS. 13A-13B are series of graphs illustrating that Th-1 cytokines are preferentially secreted by T cells electroporated with PDA-C4-27Z RNA in response to FR(+) (FIG. 13A), but not FR(−) tumor cells (FIG. 13B).
Figure 13B:
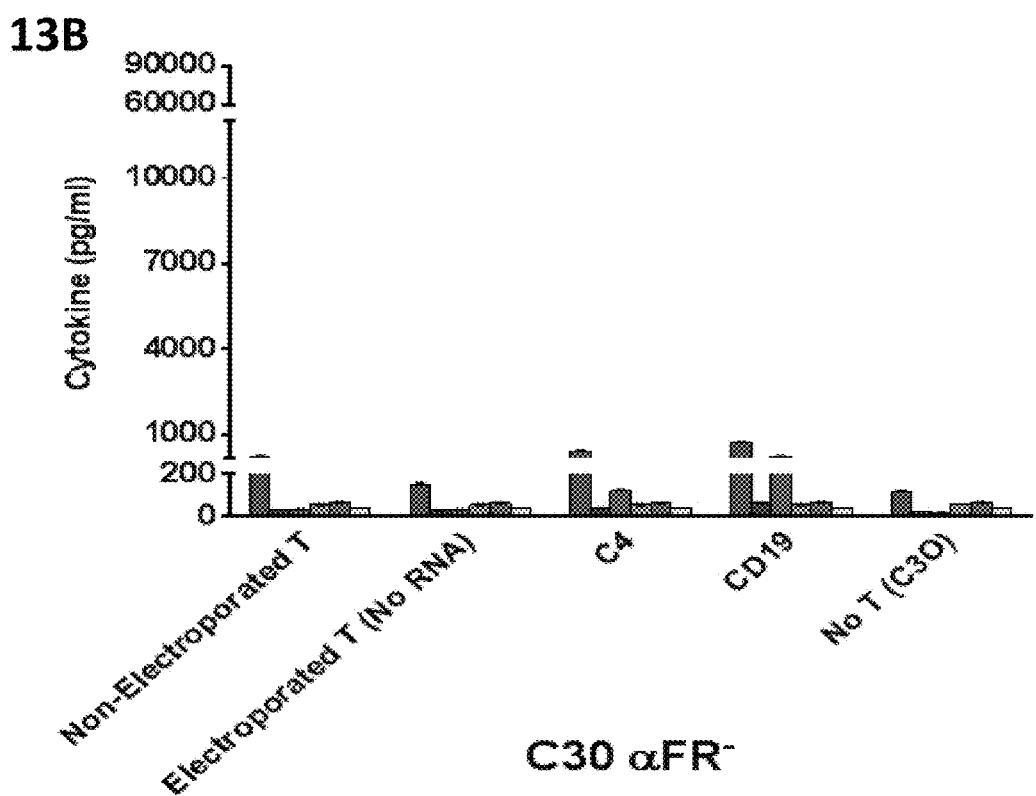

In FIGS. 13A-13B, data are presented that establish that Th-1 cytokines are preferentially secreted by T cells electroporated with PDA-C4-27Z RNA in response to SKOV3 αFR⁺ but not C30 αFR⁺ tumor cells. In sum, cell-free supernatant was harvested after 24 hrs of co-incubation of electroporated PDA-C4-27Z CAR T cells with SKOV3 or C30 at 1:1 ratio ($10^5$:$10^5$ cells), and the indicated cytokines were measured by human cytometric bead array (CBA) according to manufacturer's instructions (BD, San Diego, Calif.). Results are expressed as a mean+/−SEM of 3 independent experiments, student t-test, ***p<0.001.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A chimeric antigen receptor (CAR) comprising a fully human FRα antibody or an FRα-binding fragment thereof, an intracellular domain of a costimulatory molecule, and a CD3 zeta signaling domain, wherein the intracellular domain of the costimulatory molecule is a CD27 costimulatory domain comprising the amino acid sequence of SEQ ID NO: 9, and wherein the fully human FRα-binding fragment comprises the amino acid sequence of SEQ ID NO: 5.

2. A chimeric antigen receptor (CAR) comprising a fully human FRα-binding fragment, an intracellular domain of a costimulatory molecule, and a CD3 zeta signaling domain, wherein the intracellular domain of the costimulatory molecule is a CD27 costimulatory domain comprising the amino acid sequence of SEQ ID NO: 9, and wherein the CAR comprises the amino acid sequence of SEQ ID NO: 1.

3. The CAR of claim 1, wherein the fully human FRα antibody or the FRα-binding fragment thereof is a Fab or a scFv.

4. The CAR of claim 1, wherein the CD3 zeta signaling domain comprises the amino acid sequence of SEQ ID NO: 11.

5. The CAR of claim 1, further comprising a transmembrane domain.

6. The CAR of claim 1, further comprising a ligand that specifically binds with CD83.

7. A chimeric antigen receptor (CAR), wherein the CAR comprises the amino acid sequence of SEQ ID NO: 1.

8. The CAR of claim 7, further comprising a ligand that specifically binds with CD83.

9. A genetically modified immune cell comprising a chimeric antigen receptor (CAR), the CAR comprising a fully human FRα antibody or an FRα binding fragment thereof, an intracellular domain of a costimulatory molecule, and a CD3 zeta signaling domain, wherein the intracellular domain of the costimulatory molecule is a CD27 costimulatory domain comprising the amino acid sequence of SEQ ID NO: 9, and wherein the fully human FRα-binding fragment comprises the amino acid sequence of SEQ ID NO: 5.

10. The immune cell of claim 9, wherein the fully human FRα antibody or the FRα-binding fragment thereof is a Fab or a scFv.

11. The immune cell of claim 9, wherein the CD3 zeta signaling domain comprises the amino acid sequence of SEQ ID NO: 11.

12. The immune cell of claim 9, the CAR further comprising a transmembrane domain.

13. The immune cell of claim 9, further comprising a ligand that specifically binds with CD83.

14. The immune cell of claim 9, wherein the immune cell is a T-cell.

15. A vector comprising a nucleic acid sequence encoding a chimeric antigen receptor (CAR), the CAR comprising a fully human FRα antibody or a FRα binding fragment thereof, an intracellular domain of a costimulatory molecule, and a CD3 zeta signaling domain, wherein the intracellular domain of the costimulatory molecule is a CD27 costimulatory domain comprising the amino acid sequence of SEQ ID NO: 9, and wherein the FRα binding fragment comprises the amino acid sequence of SEQ ID NO: 5.

16. The vector of claim 15, wherein the fully human FRα antibody or the FRα-binding fragment thereof is a Fab or a scFv.

17. The vector of claim 15, wherein the CD3 zeta signaling domain comprises the amino acid sequence of SEQ ID NO: 11.

18. The vector of claim 15, the CAR further comprising a transmembrane domain.

19. The vector of claim 15, further comprising a ligand that specifically binds with CD83.

20. The vector of claim 15, wherein the vector is in an immune cell.

21. The vector of claim 20, wherein the immune cell is a T cell.

* * * * *

UNITED STATES PATENT AND TRADEMARK OFFICE
CERTIFICATE OF CORRECTION

| | | |
|---|---|---|
| PATENT NO. | : 10,844,117 B2 | Page 1 of 1 |
| APPLICATION NO. | : 15/449274 | |
| DATED | : November 24, 2020 | |
| INVENTOR(S) | : Daniel J. Powell, Jr. et al. | |

It is certified that error appears in the above-identified patent and that said Letters Patent is hereby corrected as shown below:

On the Title Page

Item (12) delete "Powell, Jr." and insert -- Powell, Jr., et al. --

Item 72 should be changed to:
-- (72) Inventors: Daniel J. Powell, Jr., Bala Cynwyd, PA (US); Silvana Canevari, Milan (IT); Mariangela Figini, Milan (IT) --

Signed and Sealed this
Seventeenth Day of September, 2024

Katherine Kelly Vidal
*Director of the United States Patent and Trademark Office*